(12) United States Patent
Britton et al.

(10) Patent No.: US 8,572,059 B2
(45) Date of Patent: Oct. 29, 2013

(54) SURVEILLANCE, MONITORING AND REAL-TIME EVENTS PLATFORM

(76) Inventors: Colin P. Britton, Lexington, MA (US);
Howard Greenblatt, Wayland, MA (US); Alan Greenblatt, Sudbury, MA (US)

(*) Notice: Subject to any disclaimer, the term of this patent is extended or adjusted under 35 U.S.C. 154(b) by 360 days.

(21) Appl. No.: 10/886,515

(22) Filed: Jul. 7, 2004

(65) Prior Publication Data
US 2005/0055330 A1    Mar. 10, 2005

Related U.S. Application Data

(63) Continuation-in-part of application No. 10/680,049, filed on Oct. 7, 2003, now Pat. No. 6,954,749, and a continuation-in-part of application No. 09/917,264, filed on Jul. 27, 2001, now Pat. No. 7,058,637, and a continuation-in-part of application No. 10/051,619, filed on Oct. 29, 2001, now Pat. No. 6,856,992, and a continuation-in-part of application No. 10/302,764, filed on Nov. 21, 2002, now Pat. No. 6,925,457, and a continuation-in-part of application No. 10/302,727, filed on Nov. 21, 2002, now Pat. No. 7,302,440, and a continuation-in-part of application No. 10/138,725, filed on May 3, 2002, now abandoned.

(60) Provisional application No. 60/485,200, filed on Jul. 7, 2003, provisional application No. 60/416,616, filed on Oct. 7, 2002, provisional application No. 60/291,185, filed on May 15, 2001, provisional application No. 60/324,037, filed on Sep. 21, 2001, provisional application No. 60/332,053, filed on Nov. 21, 2001, provisional application No. 60/332,219, filed on Nov. 21, 2001.

(51) Int. Cl.
*G06F 17/30* (2006.01)

(52) U.S. Cl.
USPC ........................................................ 707/705

(58) Field of Classification Search
USPC ..................................................... 707/1, 705
See application file for complete search history.

(56) References Cited

U.S. PATENT DOCUMENTS

| | | | |
|---|---|---|---|
| 4,701,130 A | 10/1987 | Whitney et al. | |
| 4,895,518 A | 1/1990 | Arnold et al. | |

(Continued)

FOREIGN PATENT DOCUMENTS

| | | |
|---|---|---|
| GB | 2343763 A | 5/2000 |
| WO | WO 97/22096 | 6/1997 |

(Continued)

OTHER PUBLICATIONS

Epoch Modeling Methodology : http://delivery.acm.org/10.1145/1190000/1183574/p25-shankar.pdf?key1=1183574&key2=2263555521&coll=GUIDE&dl=GUIDE&CFID=56510413&CFTOKEN=32815891.*

(Continued)

*Primary Examiner* — Hosain Alam
*Assistant Examiner* — Johnese Johnson

(57) ABSTRACT

Systems and methods according to the invention provide a surveillance, monitoring and real-time events platform to (i) enable the integration and communication of information between government agencies and organizations specifically tasked with ensuring the security and safety of our nation and its communities, (ii) to integrate information systems from federal, state and/or local agencies (from disparate data sources if necessary) in order to obtain a single, real-time view of the entire organization, and (iii) to extract more complete, actionable information from their existing systems, thereby dramatically improving decision making speed and accuracy.

34 Claims, 17 Drawing Sheets

(56) References Cited

U.S. PATENT DOCUMENTS

| | | |
|---|---|---|
| 4,953,106 A | 8/1990 | Gansner |
| 5,119,465 A | 6/1992 | Jack et al. |
| 5,129,043 A | 7/1992 | Yue |
| 5,199,068 A | 3/1993 | Cox |
| 5,259,766 A | 11/1993 | Sack et al. |
| 5,267,865 A | 12/1993 | Lee et al. |
| 5,270,920 A | 12/1993 | Pearse et al. |
| 5,301,270 A | 4/1994 | Steinberg et al. |
| 5,310,349 A | 5/1994 | Daniels et al. |
| 5,311,422 A | 5/1994 | Loftin et al. |
| 5,326,270 A | 7/1994 | Ostby et al. |
| 5,333,254 A | 7/1994 | Robertson |
| 5,339,390 A | 8/1994 | Robertson |
| 5,374,932 A | 12/1994 | Wyschogrod |
| 5,379,387 A | 1/1995 | Carlstedt |
| 5,381,332 A | 1/1995 | Wood |
| 5,395,243 A | 3/1995 | Lubin et al. |
| 5,421,730 A | 6/1995 | Lasker, III et al. |
| 5,450,480 A | 9/1995 | Man |
| 5,463,682 A | 10/1995 | Fisher |
| 5,499,293 A | 3/1996 | Behram et al. |
| 5,519,618 A | 5/1996 | Kastner |
| 5,548,506 A | 8/1996 | Srinivasan |
| 5,579,486 A | 11/1996 | Oprescu |
| 5,597,312 A | 1/1997 | Bloom et al. |
| 5,608,789 A | 3/1997 | Fisher |
| 5,634,053 A | 5/1997 | Noble et al. |
| 5,655,118 A | 8/1997 | Heindel et al. |
| 5,732,192 A | 3/1998 | Malin |
| 5,745,753 A | 4/1998 | Mosher, Jr. |
| 5,761,063 A | 6/1998 | Jannette et al. |
| 5,765,140 A | 6/1998 | Knudson et al. |
| 5,788,504 A | 8/1998 | Rice et al. |
| 5,795,155 A | 8/1998 | Morrel-Samuels |
| 5,809,212 A | 9/1998 | Shasha |
| 5,822,780 A | 10/1998 | Schutzman |
| 5,826,077 A | 10/1998 | Blakeley et al. |
| 5,826,252 A | 10/1998 | Wolters, Jr. et al. |
| 5,829,983 A | 11/1998 | Koyama et al. |
| 5,832,483 A | 11/1998 | Barker |
| 5,841,673 A | 11/1998 | Kobayashi |
| 5,873,076 A | 2/1999 | Barr et al. |
| 5,875,441 A | 2/1999 | Nakatsuyama et al. |
| 5,881,269 A | 3/1999 | Dobbelstein |
| 5,907,837 A | 5/1999 | Ferrel et al. |
| 5,935,249 A | 8/1999 | Stern et al. |
| 5,974,441 A | 10/1999 | Rogers et al. |
| 5,974,443 A | 10/1999 | Jeske |
| 5,983,267 A | 11/1999 | Shklar et al. |
| 5,987,415 A | 11/1999 | Breese et al. |
| 5,995,958 A | 11/1999 | Xu |
| 6,012,098 A | 1/2000 | Bayeh et al. |
| 6,035,412 A | 3/2000 | Tamer et al. |
| 6,044,373 A | 3/2000 | Gladney et al. |
| 6,044,466 A | 3/2000 | Anand |
| 6,078,982 A | 6/2000 | Du et al. |
| 6,085,188 A | 7/2000 | Bachmann et al. |
| 6,094,652 A | 7/2000 | Faisal |
| 6,122,632 A | 9/2000 | Botts et al. |
| 6,125,363 A | 9/2000 | Buzzeo et al. |
| 6,130,679 A | 10/2000 | Chen |
| 6,137,797 A | 10/2000 | Bass et al. |
| 6,144,997 A | 11/2000 | Lamming et al. |
| 6,151,595 A | 11/2000 | Pirolli |
| 6,151,624 A | 11/2000 | Teare |
| 6,154,738 A | 11/2000 | Call |
| 6,177,932 B1 | 1/2001 | Galdes |
| 6,182,085 B1 | 1/2001 | Eichstaedt et al. |
| 6,185,516 B1 | 2/2001 | Hardin |
| 6,185,534 B1 | 2/2001 | Breese |
| 6,212,502 B1 | 4/2001 | Ball |
| 6,240,417 B1 | 5/2001 | Eastwick et al. |
| 6,243,713 B1 | 6/2001 | Nelson et al. |
| 6,246,320 B1 * | 6/2001 | Monroe .................. 340/506 |
| 6,266,668 B1 | 7/2001 | Vanderveldt et al. |
| 6,308,163 B1 | 10/2001 | Du et al. |
| 6,330,554 B1 | 12/2001 | Altschuler |
| 6,341,277 B1 | 1/2002 | Coden et al. |
| 6,360,330 B1 | 3/2002 | Mutalik et al. |
| 6,369,819 B1 | 4/2002 | Pitkow |
| 6,381,738 B1 | 4/2002 | Choi |
| 6,389,429 B1 | 5/2002 | Kane et al. |
| 6,389,460 B1 | 5/2002 | Stewart et al. |
| 6,393,423 B1 | 5/2002 | Goedken |
| 6,405,211 B1 | 6/2002 | Sokol et al. |
| 6,405,251 B1 | 6/2002 | Bullard |
| 6,415,283 B1 | 7/2002 | Conklin |
| 6,418,413 B2 | 7/2002 | DeMarcken et al. |
| 6,418,448 B1 | 7/2002 | Sarkar |
| 6,427,151 B1 | 7/2002 | Chan et al. |
| 6,429,870 B1 | 8/2002 | Chen |
| 6,437,799 B1 | 8/2002 | Shinomi |
| 6,446,200 B1 | 9/2002 | Ball |
| 6,446,256 B1 | 9/2002 | Hyman et al. |
| 6,463,440 B1 | 10/2002 | Hind et al. |
| 6,496,833 B1 | 12/2002 | Goldberg et al. |
| 6,509,898 B2 | 1/2003 | Chi |
| 6,529,899 B1 | 3/2003 | Kraft et al. |
| 6,530,079 B1 | 3/2003 | Midkiff |
| 6,539,374 B2 | 3/2003 | Jung |
| 6,542,912 B2 | 4/2003 | Meltzer |
| 6,546,406 B1 | 4/2003 | DeRose et al. |
| 6,556,983 B1 | 4/2003 | Altschuler et al. |
| 6,571,222 B1 | 5/2003 | Matsumoto et al. |
| 6,577,769 B1 | 6/2003 | Kenyon |
| 6,583,800 B1 | 6/2003 | Ridgley |
| 6,594,662 B1 | 7/2003 | Sieffert et al. |
| 6,598,043 B1 | 7/2003 | Baclawski |
| 6,606,613 B1 | 8/2003 | Altschuler |
| 6,625,657 B1 | 9/2003 | Bullard |
| 6,636,848 B1 | 10/2003 | Aridor et al. |
| 6,640,284 B1 | 10/2003 | Shaw et al. |
| 6,643,638 B1 | 11/2003 | Xu |
| 6,643,652 B2 * | 11/2003 | Helgeson et al. ............... 707/10 |
| 6,678,679 B1 | 1/2004 | Bradford |
| 6,701,314 B1 * | 3/2004 | Conover et al. .................. 707/7 |
| 6,721,747 B2 | 4/2004 | Lipkin |
| 6,725,227 B1 | 4/2004 | Li |
| 6,751,663 B1 | 6/2004 | Farrell |
| 6,757,708 B1 | 6/2004 | Craig et al. |
| 6,772,148 B2 | 8/2004 | Baclawski |
| 6,778,971 B1 | 8/2004 | Altschuler |
| 6,792,420 B2 | 9/2004 | Stephen Chen et al. |
| 6,804,688 B2 | 10/2004 | Kobayashi et al. |
| 6,901,438 B1 | 5/2005 | Davis et al. |
| 6,925,457 B2 | 8/2005 | Britton et al. |
| 6,934,702 B2 | 8/2005 | Faybishenko et al. |
| 7,047,411 B1 | 5/2006 | DeMello et al. |
| 7,117,260 B2 | 10/2006 | Bimson et al. |
| 7,171,415 B2 | 1/2007 | Kan et al. |
| 7,289,793 B2 | 10/2007 | Norwood et al. |
| 7,313,588 B1 | 12/2007 | Shotton, Jr. et al. |
| 2001/0047355 A1 * | 11/2001 | Anwar .............................. 707/5 |
| 2002/0049603 A1 | 4/2002 | Mehra |
| 2002/0049788 A1 | 4/2002 | Lipkin et al. |
| 2002/0059566 A1 | 5/2002 | DelCambre et al. |
| 2002/0069134 A1 | 6/2002 | Solomon |
| 2002/0078030 A1 | 6/2002 | Iwayama et al. |
| 2002/0091678 A1 | 7/2002 | Miller et al. |
| 2002/0091710 A1 | 7/2002 | Dunham et al. |
| 2002/0091835 A1 | 7/2002 | Lentini et al. |
| 2002/0118688 A1 | 8/2002 | Jagannathan |
| 2002/0120598 A1 | 8/2002 | Shadmon et al. |
| 2002/0133502 A1 * | 9/2002 | Rosenthal et al. ......... 707/104.1 |
| 2002/0143759 A1 | 10/2002 | Yu |
| 2002/0178232 A1 | 11/2002 | Ferguson |
| 2003/0004934 A1 | 1/2003 | Qian |
| 2003/0009239 A1 | 1/2003 | Lombardo |
| 2003/0037145 A1 | 2/2003 | Fagan |
| 2003/0050834 A1 | 3/2003 | Caplan |
| 2003/0050927 A1 | 3/2003 | Hussam |
| 2003/0050929 A1 | 3/2003 | Bookman et al. |
| 2003/0061209 A1 | 3/2003 | Raboczi et al. |
| 2003/0074352 A1 | 4/2003 | Raboczi et al. |

(56) References Cited

U.S. PATENT DOCUMENTS

| | | | |
|---|---|---|---|
| 2003/0074369 A1 | 4/2003 | Schuetze et al. | |
| 2003/0088639 A1 | 5/2003 | Lentini et al. | |
| 2003/0109951 A1 | 6/2003 | Hsiung et al. | |
| 2003/0229529 A1 | 12/2003 | Mui et al. | |
| 2004/0024616 A1* | 2/2004 | Spector et al. | 705/2 |
| 2004/0034651 A1 | 2/2004 | Gupta et al. | |
| 2004/0054690 A1* | 3/2004 | Hillerbrand et al. | 707/104.1 |
| 2005/0055330 A1 | 3/2005 | Britton et al. | |
| 2005/0059566 A1 | 3/2005 | Brown et al. | |
| 2005/0060372 A1 | 3/2005 | DeBettencourt et al. | |
| 2005/0125683 A1 | 6/2005 | Matsuyama et al. | |
| 2006/0271563 A1 | 11/2006 | Angelo et al. | |

FOREIGN PATENT DOCUMENTS

| | | |
|---|---|---|
| WO | WO 98/05018 | 2/1998 |
| WO | WO 98/10399 | 3/1998 |
| WO | WO 98/24020 | 6/1998 |
| WO | WO 99/27460 | 6/1999 |

OTHER PUBLICATIONS

"Inkling: RDF Query Using SquishQL," downloaded from http://swordfish.rdfweb.org/rdfquery/ on Mar. 20, 2003, 2 pages.

"rdfDB Query Language", downloaded from http://www.guha.com/rdfdb/query.html on Mar. 20, 2003, 4 pages.

"RDQL—RDF Data Query Langauge," Hewlett-Packard Company, © 1994-2003, downloaded from http://www.hpl.hp.com/semweb/rdql.htm on Mar. 20, 2003, 3 pages.

Berniers-Lee et al. RFC 2396: Uniform Resouece Identifiers (URI): Generic Syntax (Aug. 1998) http://www.cs.tut.fi/~jkorpela/rfc/2396/full.html, 23 pages, downloaded on Feb. 20, 2003.

Forgy, Charles L. "Rete: A Fast Algorithm for the Many Pattern/Many Object Pattern Match Problem," Artificial Intelligence vol. 19 (1982) pp. 17-37.

Melnik, Sergey, "Storing RDF in a relational database," http://www-db.stanford.edu/~melnik/rdf/db.html, 5 pages, downloaded Feb. 20, 2003.

Quinlan, J.R., "Induction of Decision Trees," Machine Learning vol. 1 (1986) pp. 18-106.

Resource Description Framework (RDF) Model and Syntax Specification W3C Recommendation (Feb. 22, 1999) http://www.w3.org.TR/1999/REC-rdf-syntax-19990222/, 34 pages, downloaded on Feb. 20, 2003.

"The Rete Algorithm," http://herzberg.ca.sandia.gov/jess/docs/52/rete.html, 3 pages, dowloaded on Feb. 20, 2003.

Card et al., "Readings in Information Visulaizing Using Vision to Think", 1999, Morgan Kaufmann, p. 298.

"The Surveillance and Monitoring Component of the Public Health Information Network", website for the Centers for Disease Control and Prevention, http://www.cdc.gov/nedss, printed Nov. 14, 2005, 2 pages.

"An Overview of the NEDSS Initiative", website for the Centers for Disease Control and Prevention, http://www.cdc.gov/nedss/About/overview.html, printed Nov. 14, 2005, 2 pages.

"Background on Public Health Surveillance", website for the Centers for Disease Control and Prevention, http://www.cdc.gov/nedss/About/purpose.htm, printed Nov. 14, 2005, 3 pages.

"Description of the NEDSS Base System," Mar. 28, 2001, 5 pages.

"NEDSS Base System Fact Sheet", website for the Centers for Disease Control and Prevention, 2 pages.

"NEDSS Logical Data Model (NLDM) Overview and Users' Guide", Version 1.0, 92 pages.

"NEDSS Systems Architecture", Version 2.0, Apr. 15, 2001, 5 pages.

"NEDSS and NEDSS PAMs Business Discovery Statement", Version 1.2, Mar. 9, 2002, 23 pages.

"Overview of PHIN", Centers for Disease Control and Prevention website, http://www.cdc.gov/phin, printed Jan. 18, 2005, 3 pages.

"Public Health Information Network", The Association of State and Territorial Health Officials website, http://www.astho.org/?template=public_health_info_network.html, printed Jan. 18, 2005, 2 pages.

"Maestro™ Public Health Suite," Orion International website, http://www.orionhealth.com/maestro_overview.htm, printed Jan. 18, 2005, 3 pages.

PHIN: "Public Health Information Network Functions and Specification Version 1.2," pp. 1-56, Dec. 18, 2002.

Yasnoff, W., et al., "Public Health Informatics: Improving and Transforming Public Health in the Information Age," *Topics in Health Information Management*, vol. 21, Issue 3, pp. 44-51, Feb. 2001.

National Electronic Disease Surveillance System (NEDSS): A Standards-Based Approach to Connect Public Health and Clinical Medicine, Journal of Public Health Management and Practice, vol. 7(6), pp. 43-50, Nov. 2001.

Delcambre, L., et al., "Bundles in Captivity: An Application of Superimposed Information," Proceedings 17th International Conference on Data Engineering, vol. CONF. 17, pp. 111-120, Apr. 2-6, 2001.

Manola, F., "Towards a Richer Web Object Model," SIGMOD Record, vol. 27, No. 1, pp. 76-80, Mar. 1998.

Forgy, Charles L. "Rete: A Fast Algorithm for the Many Pattern/Many Object Pattern Match Problem," Artifical Intelligence vol. 19 (1982) pp. 17-37.

Published International Search Report (published May 24, 2007) and Written Opinion (mailed Feb. 12, 2007) for PCT/US05/005725.

Robert Churchill et al. RDF Technical Overview. Mozilla.org. Last Modified 11, 1999. Retrieved from: http://www.mozilla.org/rdf/doclapi.html.

Dan Brickley and Libby Miller. RDF, squish etc. Pub. on the Web Nov. 6, 2000.00. Retrieved from: http://www.itrt.bris.ac.uk/discovery/2000/11/QL/QL.txt.

Dan Brickley et al. SWIPE 0.1 specification. Pub. 2001. Retrieved from: http://rdfweb.org/2001/01/swipe/.

David Beckett. The Design and Implementation of the Redland RDF Application Framework. Copyright WWWO1 May 2-5, 2001. Retrieved from: http://www10.org/cdrom/papers/490/.

Sergey Melnik et al. Representing Order in RDF. Pub. Jan. 7, 2001. Retrieved from:http://infolab.stanford.edu/~stefan/daml/order.html.

Mathew Gray. HIVE. Semantic Labeling. May 14, 1999. Retrieved from: http://hive.sourceforge.net/mkgray-thesis/html/node8.html.

Libby Miller. Aggregating Recommendations using RDF. ILRT. Org. Pub. Jan. 10, 1999.

Larry Kerschberg. Knowledge Management in Heterogeneous Data Warehouse Environments. Pub. 2001.

Gregory Karvounarakis et al. Querying Community Web Portals. Sigmod Pub. Pub. 2000.

Bernd Amann et al. Integrating ontologies and thesauri for RDF schema creation and metadata querying. Mar. 6, 2001.

Resource Description Framework (RDF) Model and Syntax Specification. W3C Recommendation. Feb. 22, 1999.

Supplemental European Search Report dated Aug. 21, 2007 (5 pages).

Miller, Eric et al., RDF Primer, W3C @@ Editor's Draft Jan. 27, 2002 @@, Copyright 2001, 2002 (MIT,INRIA, Keio) (22 pages).

Six, Janet, M. et al, "Effective e Graph Visualization Via Node Grouping", Proceedings of the IEEE Symposium on Information Visualization 2001 (INFOVIS'01) (8 pages).

Gandon, Fabien et al. "A Multi-Agent System to Support Exploiting an XML-based Corporate Memory" INRIA, ACACI Project, 2004 Route des Lucioles, 06902 Sophia Antipolis, France, Proc. of the Third Int. Conf. on Practical Aspects of Knowledge Management (PAKM2000) Basel, Swwitzerland, Oct. 30-31, 2000, (U.Reimer, ed.).

United States Patent and Trademark Office Action for U.S. Appl. No. 11/245,994 dated Aug. 29, 2008.

United States Patent and Trademark Office Action for U.S. Appl. No. 11/245,994 dated Dec. 12, 2007.

United States Patent and Trademark Office Action for U.S. Appl. No. 11/064,438 dated Apr. 29, 2009.

United States Patent and Trademark Office Action for U.S. Appl. No. 11/064,438 dated Aug. 12, 2008.

(56) References Cited

OTHER PUBLICATIONS

United States Patent and Trademark Office Action for U.S. Appl. No. 11/064,438 dated Oct. 9, 2007.
Thompson, Craig "Workshop on Compositional Software Architectures Workshop Report," Software Engineering Notes, vol. 23. No. 3, May 1998.
Takeda, Koichi, "Site Outlining," IBM Research, Tokyo Research Lab, 1623-14; Mar. 1998.
Bucher, Alex et al. "Discovering Internet Marketing Intelligence through Online Analytical Web Usage Mining," SIGMOD Record, vol. 27, No. 4, Dec. 1998.
Ouksel, Aris et al. "Semantic Interoperability in Global Information Systems," SIGMOD Record, vol. 28, No. 1, Mar. 1999.
Sycara, Katia et al. "Dynamic Service Matchmaking Among Agents in Open Information," SIGMOD Record, vol. 28, No. 1, Mar. 1999.
Buneman et al "Interaction between Path and Type Constraints", Proceedings of ACM Symposium on Principles of Database Systems, 1999, pp. 56-67.
Swick, Ralph, "RDF:Weaving the Web of Discovery: Putting it Together," netWorker archive, vol. 3 , Issue 2 (Jun. 1999) , pp. 21-25 , Year of Publication: 1999 , ISSN:1091-3556.
Suciu, Dan "Managing Web Data," ACM SIGMOD Record archive, vol. 28 , Issue 2 (Jun. 1999), p. 510 , Year of Publication: 1999, ISSN:0163-5808.
Crestani, Fabio "Vocal Access to a Newspaper Archive: Design Issues and Preliminary Investigations," International Computer Science Institute; Mar. 1999.
McGrath et al, "Digital Library Technology for Locating and Accessing Scientific Data," International Conference on Digital Libraries , Proceedings of the fourth ACM conference on Digital libraries , Berkeley, California, United States , pp. 188-194 , Year of Publication: 1999. ISBN:1-58113-145-3.
Thomas Lee, et al "Information integration with attribution support for corporate profiles," Information integration with attribution support for corporate profiles, Conference on Information and Knowledge Management, Proceedings of the eighth international conference on Information and knowledge management , Kansas City, Missouri, United States , pp. 423-429 ,Year of Publication: 1999 , ISBN:1-58113-146-1.
Tudhope et al "Semantically Indexed Hypermedia: Linking Information Disciplines," ACM Computing Surveys (CSUR), vol. 31 , Issue 4es (Dec. 1999), Article No. 4, Year of Publication: 1999 , ISSN:0360-0300.
Bonifati, "Comparative Analysis of Five XML Query Languages," SIGMOD Record, vol. 29, No. 1, Mar. 2000.
Carr, Leslie et al. "The Evolution of Hypertext Link Services," ACM Computing Surveys, vol. 31, No. 4es, Dec. 1999.
Fan, Wenfei, "Integrity Constraints for XML," ACM Symposium on Principles of Database Systems archive Proceedings of the nineteenth ACM SIGMOD-SIGACT-SIGART symposium on Principles of database systems; Dallas, Texas, United States; pp. 23-34 ; Year of Publication: 2000.
Chen, James et al "A Distributed Multi-Agent System for Collaborative Information Management and Sharing," RBAC 2000, Berlin, Germany ISBN 1-58113-259-x/00/07; 2000.
Melnik, Sergey "A Mediation Infrastructure for Digital Library Services," Digital Libraries, San Antonio, TX ACM 2000 -581 13-231 x/00/0006; 2000.
Melnik, Sergey "Building a Distributed Full-Text Index of the Web," WWW10, May 1-5, 2001, Hong Kong ACM 1-58113-348-0/01/00005.
Conference Review Department, "Semantic Web Workshop: Models, Architectures and Management of Sep. 21, 2000" Intelligence, Summer 2001, pp. 39-44.
Brickley, Dan "Semantic Web History: Nodes and Arcs 1989-1999," The WWW Proposal and RDF, revised Mar. 2001 http:www.w3.org/1999/11/11-WWWProposal/.
Halpin, Harry et al "W3C Semantic Web Activity," W3C Sematic Web, http://www.w3.org/2001/sw/: last updated Apr. 6, 2009, copyright 1994-2009.
Prudhommeaux, Eric "Check and Visualize your RDF," W3C website, Feb. 15, 2007, http://www.w3.org/RDF/Validator/.
RDF Interest Group 1999-2004, available at W3C Semantic Web, http://www.w3.org/RDF/Interest/ ; last updated Dec. 8, 2005; downloaded Apr. 2009.
Berners-Lee, Tim "Information Management: A Proposal," Mar. 1989 and May 1990; 14 pages.
Beckett, Dave Dave Beckett's Resource Description Framework (RDF) Resource Guide, available at http://planetrdf.com/guide, last updated Sep. 23, 2005, 26 pages.
Brickley, Dan "RDF Query in Javascript demo," W3C website, Jul. 28, 2001, http://www.w3.org/1999/11/11-WWWProposal/rdfqdemo.html.
Extensible Markup Language (XML), W3C Sematic Web, http://www.w3.org/XML/ ; last updated Apr. 5, 2009; copyright 1996-2003; 5 pages.
Berniers-Lee et al, "The Enquire Manual," Oct. 1980, http://infomesh.net/2001/enquire/manual/.
Dublin Core Metadata Initiative, available at http://dublincore.org, web page last updated Mar. 31, 2009, copyright 1995-2009; 1 page.
Resource Description Framework, (RDF) Schema Specification, W3C Proposed Recommendation Mar. 3, 1999, http://www.w3.org/TR/1999/PR-rdf-schema-19990303/.
Berners-Lee et al "Web Architecture: Describing and Exchanging Data," W3C Recommendations, Jun. 7, 1999, http://www.w3.org/1999/06/07-WebData.
Berners-Lee, "Semantic Web Road Map," W3C Recommendations, Sep. 1998, http://www.w3.org/DesignIssues/Semantic.html.
Lassila, et al "Resource Description Framework (RDF) Model and Syntax Specification," W3C Recommendations, Feb. 22, 1999.
Berners-Lee, "What a semantic web can represent," W3C Recommendations, Sep. 1998.
Fensel, D. "Ontobroker: Or How to Enable Intelligent Access to the WWW," Proceedings of the 11th Banff Knowledge Acquisition for Knowledge-Based System Workshop (KAW98), Banaff, Kanada, Apr. 1998.
Swick, R. "The Cambridge Communique," W3C Recommendations, Oct. 1999, http://www.w3.org/TR/schema-arch.
Technical Reports and Communications, W3C website, http://www.w3.org/TR/ ; last updated Apr. 21, 2009; copyrighted 1994-2006.
Bray, Tim et al. "Extensible Markup Language," W3C Recommendations, Feb. 10, 1998, http://www.w3.org/TR/1998/REC-xml-19980210.
Cowan, John et al. "XML Information Set," W3C Recommendations, May 17, 1999, http://www.w3.org/TR/1999/WD-xml-infoset-19990517.
Extensible Markup Language Activity Statement , W3C Ubiquitous Web, http://www.w3.org/XML/Activity; downloaded Apr. 10, 2009; 3 pages.
Clark, James Editor "XSL Transformations," W3C Recommendations, Nov. 16, 1999, http://www.w3.org/TR/xslt.
Manola, Frank Editor "RDF Primer," W3C Working Draft, Mar. 2002, http://www.w3.org/TR/2002/WD-rdf-primer-20020319/.
Malhotra, Ashok et al., "XML Schema Requirements," W3C Note, Feb. 15, 1999, http://www.w3.org/TR/NOTE-xml-schema-req.
Web site; http://www.w3.org/DesignIssues/RDFnot.html ; Sep. 27, 2004 ; 8 pages.
Final Office Action from the United States Patent and Trademark Office dated Mar. 23, 2010 for U.S. Appl. No. 11/064,438 (20 Pages).
Kerstin Forsberg et al. Extensible use of RDF in a business context. Computer Networks 33 (2000), pp. 347-364: The International Journal of Computer and Telecommunications Networking . Published Jun. 2000.
S. Alexaki et al. Managing RDF Metadata for Community Webs. Springer Berlin / Heidelberg. vol. 1921/2000, pp. 140-151.
Terence Critchlow. Report on XEWA-00: the XML enabled wide-area searches for bioinformatics workshop. ACM> vol. 30 , Issue 1 (Mar. 2001).
Semantic Web Workshop 2001. Proceedings of the Second International Workshop on the Semantic Web. SemWeb'2001. S. Staab et al. Hong Kong, China, May 2001.

(56) References Cited

OTHER PUBLICATIONS

M. R. Kogalovsky. Systematization of information resources collections in digital libraries. MAIK Nauka/Interperiodica distributed exclusively by Springer Science+Business Media LLC. vol. 26, No. 3 / May 2000, pp. 140-155.

Ludascher, B. Gupta, A. Martone, M.E.Model-based mediation with domain maps. Data Engineering, 2001. Proceedings. 17$^{th}$ International Conference on Publication Date: 2001. pp. 81-90. Meeting Date: Apr. 2, 2001-Apr. 6, 2001.

Omelayenko, B., "Learning of Ontologies for the Web: the Analysis of Existent Approaches" Proceedings of the International Workshop on Web Dynamics Held in Conj. With the 8th Internationsl Conference on Database Theory Jan. 3, 2001 pp. 1-10, XP002378744, London, UK.

Nick, Z.Z. et al., "Web Search Using a Genetic Algorithm" IEEE Internet Computing, vol. 5, No. 2, Mar. 2001, pp. 18-26, XP002378745, USA.

Supplemental European Search Report for European Application No. 02736950.3 dated May 19, 2006, 4 pages.

European Patent Office Communication Pursuant to Article 96(2) for European Applicaiton No. 02741744.2, dated Dec. 8, 2006, 12 pages.

International Search Report for International Appliaction No. PCT/US05/05725, dated Feb. 12, 2007, (9 pages).

* cited by examiner

SURVEILLANCE, MONITORING AND REAL-TIME EVENTS PLATFORM

This application claims the benefit of priority of U.S. Provisional Patent Application Ser. No. 60/485,200, filed Jul. 7, 2003, entitled "Surveillance, Monitoring and Real-Time Events Platform," the teachings of which are incorporated herein by reference. This application is a continuation in part of and claims the benefit of priority of the following copending, commonly-assigned patent applications, the teachings of all of which are incorporated herein by reference: U.S. patent application Ser. No. 10/680,049, filed Oct. 7, 2003, entitled "Methods and Apparatus for Identifying Related Nodes in a Directed Graph Having Named Arcs" (now issued as U.S. Pat. No. 6,954,749); U.S. Provisional Patent Application Ser. No. 60/416,616, filed Oct. 7, 2002, entitled "Methods and Apparatus for Identifying Related Nodes in a Directed Graph Having Named Arcs"; U.S. patent application Ser. No. 09/917,264, filed Jul. 27, 2001, entitled "Methods and Apparatus for Enterprise Application Integration" (now issued as U.S. Pat. No. 7,058,637); U.S. Provisional Patent Application Ser. No. 60/291,185, filed May 15, 2001, entitled "Methods and Apparatus for Enterprise Application Integration"; U.S. patent application Ser. No. 10/051,619, filed Oct. 29, 2001, entitled "Methods and Apparatus for Real-Time Business Visibility Using Persistent Schema-Less Data Storage" (now issued as U.S. Pat. No. 6,856,992); U.S. Provisional Patent Application Ser. No. 60/324,037, filed Sep. 21, 2001, entitled "Methods and Apparatus for Real-Time Business Visibility Using Persistent Schema-Less Data Storage"; U.S. patent application Ser. No. 10/302,764, filed Nov. 21, 2002, entitled "Methods and Apparatus for Querying a Relational Data Store Using Schema-Less Queries" now published as US 2003/015841 and issued as U.S. Pat. No. 6,925,457); U.S. Provisional Patent Application Ser. No. 60/332,053, filed Nov. 21, 2001, entitled "Methods and Apparatus for Querying a Relational Database of RDF Triples in a System for Real-Time Business Visibility"; U.S. Provisional Patent Application Ser. No. 60/332,219, filed Nov. 21, 2001, entitled "Methods and Apparatus For Calculation and Reduction of Time-Series Metrics from Event Streams or Legacy Databases in a System for Real-Time Business Visibility"; U.S. patent application Ser. No. 10/302,727, filed Nov. 21, 2002, entitled "Methods and Apparatus for Statistical Data Analysis and Reduction for an Enterprise Application" (now issued as U.S. Pat. No. 7,302,440); U.S. patent application Ser. No. 10/138,725, filed May 3, 2002, entitled "Methods and Apparatus for Visualizing Relationships Among Triples of Resource Description Framework (RDF) Data Sets" (now published as U.S. Patent Publication No. 2003-0208499 A1).

BACKGROUND OF THE INVENTION

The invention pertains to surveillance, monitoring and real-time event processing. It has application in public health & bioterrorism, border and port security, public and community safety, and government data integration, to name a few.

Today, national, state, and local governments are challenged to achieve unprecedented levels of cooperation in and among agencies and organizations charged with protecting the safety of communities. Many of these organizations use either proprietary or incompatible technology infrastructures that need to be integrated in order to provide real-time, critical information for effective event monitoring and coordinated emergency response. Information must be shared instantaneously and among numerous entities to effectively identify and respond to a potential threat or emergency-related event.

Significant efforts are underway along these lines, for example, in the public health and bioterrorism arena. The Centers for Disease Control and Prevention (CDC) of the U.S. Department of Health and Human Services has launched several initiatives toward forming nationwide networks of shared health-related information that, when fully implemented, will facilitate the rapid identification of, and response to, health and bioterrorism threats. The CDC plans the Health Alert Network (HAN), for example, to provide infrastructure supporting for distribution of health alerts, disease surveillance, and laboratory reporting. The Public Health Information Network (PHIN) is another CDC initiative that will provide detailed specifications for the acquisition, management, analysis and dissemination of health-related information, building upon the HAN and other CDC initiatives, such as the National Electronic Disease Surveillance System (NEDSS).

While these initiatives, and others like them in both health and non-health-related fields, define functional requirements and set standards for interoperability of the IT systems that hospitals, laboratories, government agencies and others will use in forming the nationwide networks, they do not solve the problem of finding data processing equipment capable of meeting those requirements and standards.

It is not uncommon for a single enterprise, such as a hospital, for example, to have several separate database systems to track medical records, patient biographical data, hospital bed utilization, vendors, and so forth. The same is true of the government agencies charged with monitoring local, state and national health. In each enterprise, different data processing systems might have been added at different times throughout the history of the enterprise and, therefore, represent differing generations of computer technology. Integration of these systems at the enterprise level is difficult enough; it would be impossible on any grander scale. This is a major impediment to surveillance, monitoring and real-time events processing in public health and bioterrorism. Similar issues result in parallel problems in border and port security, public and community safety, and government data integration, is the consolidation of data from disparate databases and other sources.

An object of this invention is to provide improved methods and apparatus surveillance, monitoring and real-time events processing.

A related object is to provide such methods and apparatus as can be applied in public health and bioterrorism, e.g., to facilitate CDC initiatives in this area.

A further object of the invention is to provide such methods and apparatus as can be applied border and port security, public and community safety, and government data integration.

A still further object of the invention is to provide such methods and apparatus as can be implemented inexpensively, incrementally or otherwise without interruption of IT functions that they bring together.

SUMMARY OF THE INVENTION

To meet these challenges, systems and methods described herein provide a surveillance, monitoring and real-time events platform to (i) enable the integration and communication of information between government agencies and organizations specifically tasked with ensuring the security and safety of our nation and its communities, (ii) to integrate information systems from federal, state and/or local agencies (from disparate data sources if necessary) in order to obtain a single, real-time view of the entire organization, and (iii) to extract more complete, actionable information from their existing systems, thereby dramatically improving decision making speed and accuracy.

The platform has application in a variety of areas, including, public health & bioterrorism, border and port security, public and community safety, and government data integration, to name a few.

Public Health & BioTerrorism

Effective and timely surveillance and monitoring of health-related events is essential for early detection and management of a public health threats, whether a naturally occurring disease, such as West Nile Virus, or a biological or chemical attack. State and local public health officials must have the ability to identify the specific nature and scope of an event and launch a tightly coordinated response, all in real-time.

In one aspect of the invention, the surveillance, monitoring and real-time events platform is adapted for use, e.g., as a local, state or federal node, in a network conforming to the Public Health Information Network (PHIN) initiative of the Centers for Disease Control and Prevention (CDC) of the U.S. Department of Health and Human Services, or as an infrastructure element of that network. This provides a real-time solution that:

- Delivers a dual purpose real-time syndromic surveillance system covering both bioterrorism and targeted communicable diseases
- Transforms data from a variety of protocols (CSV, EDI, Excel, XML) into industry standard formats HL7 and HIPPA
- Integrates disparate data systems (hospitals, labs, clinics, pharmacies) from any format or location quickly and without custom coding
- Enables synchronous and asynchronous collaboration between participating departments and personnel
- Provides real-time customizable reporting and GIS mapping via web-based graphical interface
- Initiates and manages real-time notifications to first responders and public health officials via web, email, phone, wireless PDA and mobile phone
- Complies with the CDC's NEDSS, HAN and PHIN architectures Systems and methods according to this aspect of the invention are designed as for multi-purposes. They function as a real-time surveillance system, a bioterrorism detection and response system and a collaborative network for distance learning and communication.

As the CDC develops standards and mandated reporting protocols such as the National Electronic Disease Surveillance System (NEDSS), Health Alert Network (HAN) and Public Health Information Network (PHIN), it is up to state and local health officials to understand these new requirements and develop a system to comply. Systems and methods according to this aspect of the invention are designed to satisfy all NEDSS, HAN and PHIN requirements and more. They provide a platform technology that is highly flexible and scaleable meaning that it can adapt and stay current with new requirements and specifications with minimal effort. This feature allows health agencies to add data systems and functionality to the platform easily without impacting the current architecture.

Border & Port Security

Border and port security represent complex security challenges. These sites represent vulnerable points of entry and require monitoring of ocean vessel arrivals and departures, assessing potentially hazardous cargo, responding to immigration challenges, terrorist threats and managing the proximity risk to civilians and land-based targets such as nuclear facilities, dams, power plants, gas lines, and other biological and chemical facilities. Due to the complex and porous nature of borders and ports, many distinct organizations are required to work in close cooperation and effectively share critical information.

In one aspect of the invention, the surveillance, monitoring and real-time events platform is adapted for border and port security applications, providing:

- Real-time information in a secure web-based user interface
- Providing a consolidated view of port security status by integrating multiple agencies and organizations existing information systems to appear as one, in real-time.
- Integration of meteorological or other environmental information
- GIS (geo-spatial mapping) for rapid local assessment and visibility
- Time-critical risk assessment based on local, state and federal data sources
- Scenario-based event management for medical, emergency and public safety responders with immediate notifications to key safety personnel Public & Community Safety Local law enforcement agencies are increasingly involved in complex public safety issues. Today, airports, construction sites, concerts, and other large, high-profile community events require greater levels of security, including biometric identification and other methods of individual scanning and surveillance. The surveillance, monitoring and real-time events platform can be deployed in applications designed to identify community threats or security breaches in a wide range of settings including inter-agency solutions for superior security surveillance and response. This platform provides:

- Real-time reporting with secure web-based user interface enabling a single view of a multi-agency operation
- Integration of critical data from existing data sources (any data in any format) to create better public safety information
- GIS (geo-spatial mapping) for rapid local assessment and visibility
- Real-time risk assessment based on local, state and federal data sources
- Coordinated communication and immediate notifications to key safety personnel and responders Government Solution for Data Visibility Government agencies are challenged with the daunting task of improving agency-wide and inter-agency information flow and visibility, especially in today's volatile environment. True agency-wide information access for real-time analysis is only achieved by being able to tie together all existing disparate data sources, from any location, and offer a consolidated view of critical information.

In one aspect of the invention, the surveillance, monitoring and real-time events platform provides a single point of access to all state security-related IT systems (Justice Dept, Law Enforcement, Dept of Health) to expedite identifying potential threats. The platform can also provide information visibility across an organizations systems. The platform:

- Leverages investments in existing IT infrastructure
- Provides a single, comprehensive view of critical information from all data sources
- Provides a solution that is operational in a fraction of the time a "traditional" data integration project would take.
- Benefits from a flexible, scalable, interoperable platform capable of integrating any agency's data sources for optimal visibility and operational readiness The aforementioned and other aspects of the invention are evident in the drawings and in the description that follows.

BRIEF DESCRIPTION OF THE DRAWINGS

The foregoing features of this invention, as well as the invention itself, may be more fully understood from the following detailed description of the drawings in which:

FIG. 4-16 depict a visual display used in the system of FIG. 1 to call alerts and other information to the attention of the user.

DETAILED DESCRIPTION OF THE ILLUSTRATED EMBODIMENT

Figure 1:
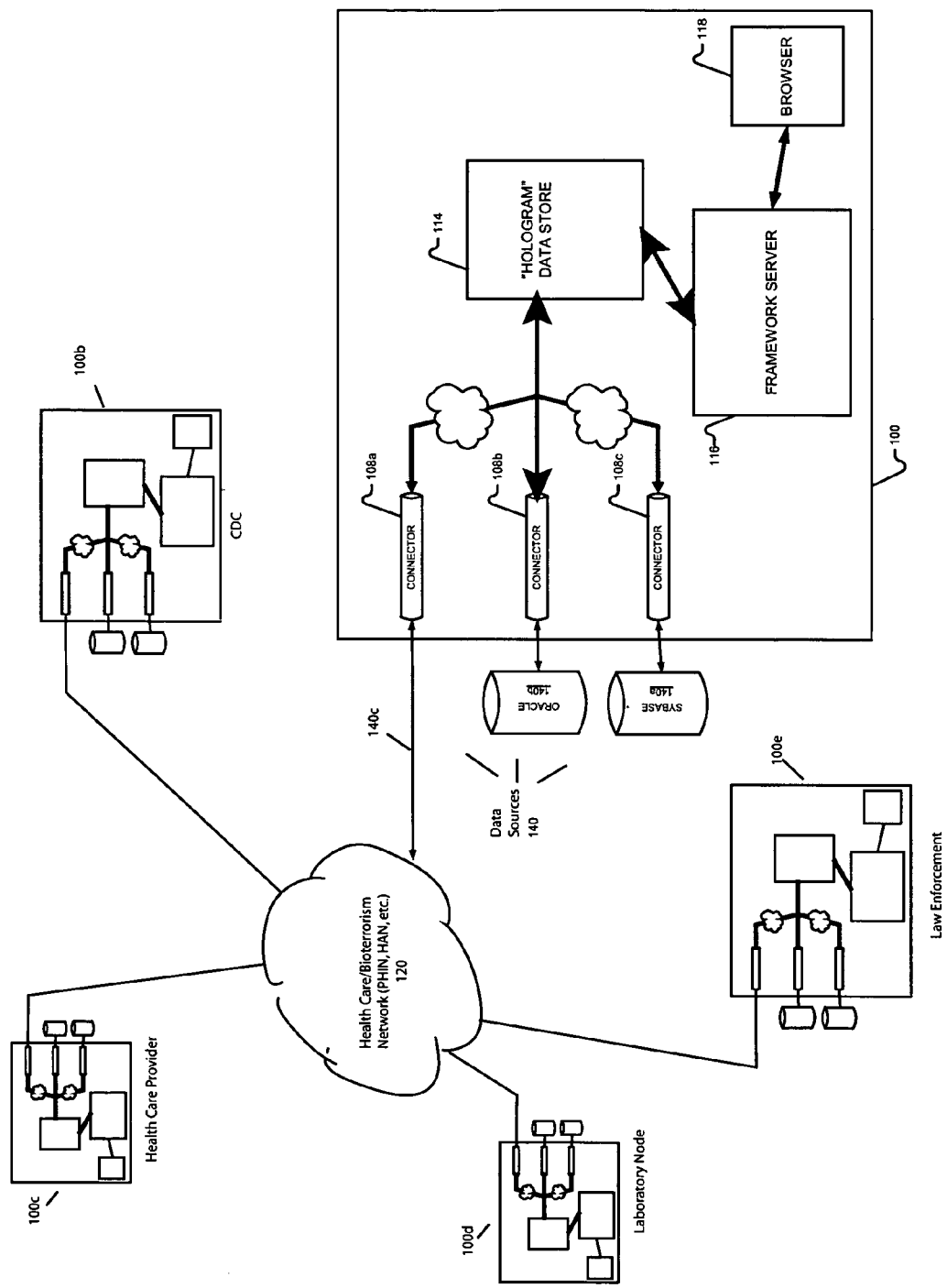
FIG. 1 depicts a surveillance, monitoring and real-time events system 100 according to the invention suitable for the adaptation to a public health & bioterrorism application, e.g., as part of PHIN, HAN or NEDSS-compatible networks.

FIG. 1 depicts a surveillance, monitoring and real-time events system 100 according to the invention suitable for the adaptation to a public health & bioterrorism application, e.g., as part of PHIN, HAN or NEDSS networks. Illustrated system 100 represents a data processing station (or stations) resident at a node in such a network, such as, for example, a clinical care provider, a laboratory, a local or state health department, the CDC headquarters, a local or national law enforcement office, or otherwise. Though the illustrated system is used in a public health & bioterrorism application, it will be appreciated that a similar such system can be applied in border & port security, public & community safety, and government data integration applications, described above, among others.

Illustrated system 100, which can be embodied in conventional digital data processing apparatus (including attendant processor(s), display units, storage units, and communications devices) of the type conventional in the art, comprises connectors 108 that provide software interfaces to legacy and other databases, data streams, and sources of information—collectively, databases 140—in clinical care facilities or other entities (such as agency field offices or laboratories), organizations (such as a governmental agencies) or enterprises, such as the PHIN network, the HAN network or otherwise. A "hologram" data store 114 (hereinafter, "data store" or "hologram data store"), which is coupled to the databases 140 via the connectors 108, stores data from those databases 140. A framework server 116 accesses the data store 114, presenting selected data to (and permitting queries from) a user browser 118. The server 116 can also permit updates to data in the data store 114 and, thereby, in the databases 140. These updates can include both the addition of new data and the modification of old data.

In the illustration, databases 140 include a database 140a maintained with a Sybase® database management system, a database 140b maintained with an Oracle® database management system. The "databases" 140 also include a data stream 140c providing information from other nodes 100b, 100c, 100d, 100e, of the PHIN, HAN, NEDSS or other network 120. Those other nodes can be constructed and operated in the manner of system 100 (as suggested in the illustration by their depiction using like silhouettes) or in any other manner consistent with PHIN, HAN, NEDSS or other network operations. The network 120 represents the Internet, wide area network or other medium or collection of media that permit the transfer of information (continuous, periodic or otherwise) between the nodes in a manner consistent with requirements of PHIN, HAN, NEDSS or other applicable network standards.

Of course, these are merely examples of the variety of databases or other sources of information with which methods and apparatus as described herein can be used. Common features of illustrated databases 140 are that they provide access to information of actual or potential interest to the node in which system 100 resides and that they can be accessed via application program interfaces (API) or other mechanisms dictated by the PHIN, HAN, NEDSS or other applicable network.

Connectors 108 serve as interfaces to databases, streams and other information sources 140. Each connector applies requests to, and receives information from, a respective database, using that database's API or other interface mechanism, e.g., as dictated by the PHIN, HAN or other otherwise. Thus, for example, connector 108a applies requests to database 140a using the corresponding SAP API; connector 108b applies requests to database 140b using the Oracle API; and connector 108c applies requests to and/or receives information from the stream or information source 140c use PHIN-appropriate, HAN-appropriate, NEDSS-appropriate or other stream or network-appropriate requests. Thus, by way of non-limiting example, the connector nector 108c can generate requests to the network 120 to obtain data from health care institutions and other nodes on the network.

The requests can be simple queries, such as SQL queries and the like (e.g., depending on the type of the underlying database and its API) or more complex sets of queries, such as those commonly used in data mining. For example, one or more of the connectors can use decision trees, statistical techniques or other query and analysis mechanisms known in the art of data mining to extract information from the databases. Specific queries and analysis methodologies can be specified by the hologram data store 114 or the framework server 116 for application by the connectors. Alternatively, the connectors themselves can construct specific queries and methodologies from more general queries received from the data store 114 or server 116. For example, request-specific items can be "plugged" into query templates thereby effecting greater speed and efficiency.

Regardless of their origin, the requests can be stored in the connectors 108 for application and/or reapplication to the respective databases 108 to provide one-time or periodic data store updates. Connectors can use expiration date information to determine which of a plurality of similar data to return to the data store, or if dates are absent, the connectors can mark returned data as being of lower confidence levels.

In a system 100 according to the invention used as part of the PHIN network, the connector 108c (and/or other functionality not shown) provides for the automated exchange of data between public health partners, as required of nodes in the PHIN network. Thus the connector nector 108c (and/or other functionality) comprises an ebXML compliant SOAP web service that can be reached via an HTTPS connection after appropriate authentication and comprises, or is coupled to, an HTTPS port. It also supports messaging in the industry standard requisite formats and message content specified by the PHIN standard. The connector 108c also provides for translation of messages received from the network 120 into a format compatible with the NEDSS and/or other requisite data models specified by the PHIN standards for storage in the data store 114 as detailed further below. And, the connector 108c (or other functionality) facilitates the exchange and management of specimen and lab result information, as required under the PHIN standard. Systems 100 according to the invention used as part of HAN or NEDSS-compatible networks provide similar functionality, as particularly required under those initiatives.

Data and other information (collectively, "messages") generated by the databases, streams and other information sources 140 in response to the requests are routed by connectors to the hologram data store 114. That other information can include, for example, expiry or other adjectival data for use by the data store in caching, purging, updating and selecting data. The messages can be cached by the connectors 108, though, they are preferably immediately routed to the store 114.

Information updates entered, for example, by a user who is accessing the store 114 via a server 116 and browser 118, are transmitted by server 116 to data store 114. There, any triples implicated by the change are created or changed in store 114C, as are the corresponding RDF document objects in store 114A. An indication of these changes can be forwarded to the respective databases, streams or other information sources 140 via the connectors 108, which utilize the corresponding API (or other interface mechanisms) to alert those sources 140 of updates. Likewise, changes made directly to the store 114C, e.g., using a WebDAV client or otherwise, can be forwarded by the connector 108 to the respective sources 140.

The hologram data store 114 stores data from the databases 140 (and from the framework server 116, as discussed below) as RDF triples. The data store 114 can be embodied on any digital data processing system or systems that are in communications coupling (e.g., as defined above) with the connectors 108 and the framework server 116. Typically, the data store 114 is embodied in a workstation or other high-end computing device with high capacity storage devices or arrays, though, this may not be required for any given implementation.

Though the hologram data store 114 may be contained on an optical storage device, this is not the sense in which the term "hologram" is used. Rather, it refers to its storage of data from multiple sources (e.g., the databases 140) in a form which permits that data to be queried and coalesced from a variety of perspectives, depending on the needs of the user and the capabilities of the framework server 116.

To this end, a preferred data store 114 stores the data from the databases 140 in subject-predicate-object form, e.g., RDF triples, though those of ordinary skill in the art will appreciate that other forms may be used as well, or instead. By way of background, RDF is a way of expressing the properties of items of data. Those items are referred to as subjects. Their properties are referred to as predicates. And, the values of those properties are referred to as objects. In RDF, an expression of a property of an item is referred to as a triple, a convenience reflecting that the expression contains three parts: subject, predicate and object.

Listed below is a portion of a data set of the type with which the invention can be practiced. The listing contains RDF triples, here, expressed in extensible markup language (XML) syntax. Those skilled in the art will, of course, appreciate that RDF triples can be expressed in other syntaxes and that the teachings hereof are equally applicable to those syntaxes. Further, the listing shows only a sampling of the triples in a data store 114, which typically would contain tens of thousands or more of such triples.

```
<rdf:RDF...xmlns="http://www.metatomix.com/postalCode/1.0#>
  <rdf:Description rdf:about="postal://zip#02886">
    <town>Warwick</town>
    <state>RI</state>
    <country>USA</country>
    <zip>02886</zip>
  <rdf:Description>
    <rdf:Description rdf:about="postal://zip#02901">
    <town>Providence</town>
    <state>RI</state>
    <country>USA</country>
    <zip>02901</zip>
  </rdf:Description>
```

Subjects are indicated within the listing using a "rdf:about" statement. For example, the second line of the listing defines a subject as a resource named "postal://zip#02886." That subject has predicates and objects that follow the subject declaration. One predicate, <town>, is associated with a value "Warwick". Another predicate, <state>, is associated with a value "RI". The same follows for the predicates <country> and <zip>, which are associated with values "USA" and "02886," respectively. Similarly, the listing shows properties for the subject "postal://zip#02901," namely, <town> "Providence," <state> "RI," <country> "US" and <zip> "02901."

In the listing, the subjects and predicates are expressed as uniform resource indicators (URIs), e.g., of the type defined in Berniers-Lee et al, *Uniform Resource Identifiers (URI): Generic Syntax* (RFC2396) (August 1998), and can be said to be expressed in a form <scheme>://<path>#<fragment>. For the subjects given in the example, <scheme> is "postal," <path> is "zip," and <fragment> is, for example, "02886" and "02901."

The predicates, too, are expressed in the form <scheme>://<path>#<fragment>, as is evident to those in ordinary skill in the art. In accord with XML syntax, the predicates in lines two, et seq., of the listing must be interpreted as suffixes to the string provided in the namespace directive "xmlns=http://www.metatomix.com/postalCode/1.0#" in line one of the listing. This results in predicates that are formally expressed as: "http://www.metatomix.com/postalCode/1.0#town," "http://www.metatomix.com/postalCode/1.0#state," "http://www.metatomix.com/postalCode/1.0#country" and "http://www.metatomix.com/postalCode/1.0#zip."

Hence, the <scheme> for the predicates is "http" and <path> is "www.metatomix.com/postalCode/1.0." The <fragment> portions are <town>, <state>, <country> and <zip>, respectively. It is important to note that the listing is in some ways simplistic in that each of its objects is a literal value. Commonly, an object may itself be another subject, with its own objects and predicates. In such cases, a resource can be both a subject and an object, e.g., an object to all "upstream" resources and a subject to all "downstream" resources and properties. Such "branching" allows for complex relationships to be modeled within the RDF triple framework.

Figure 2A:
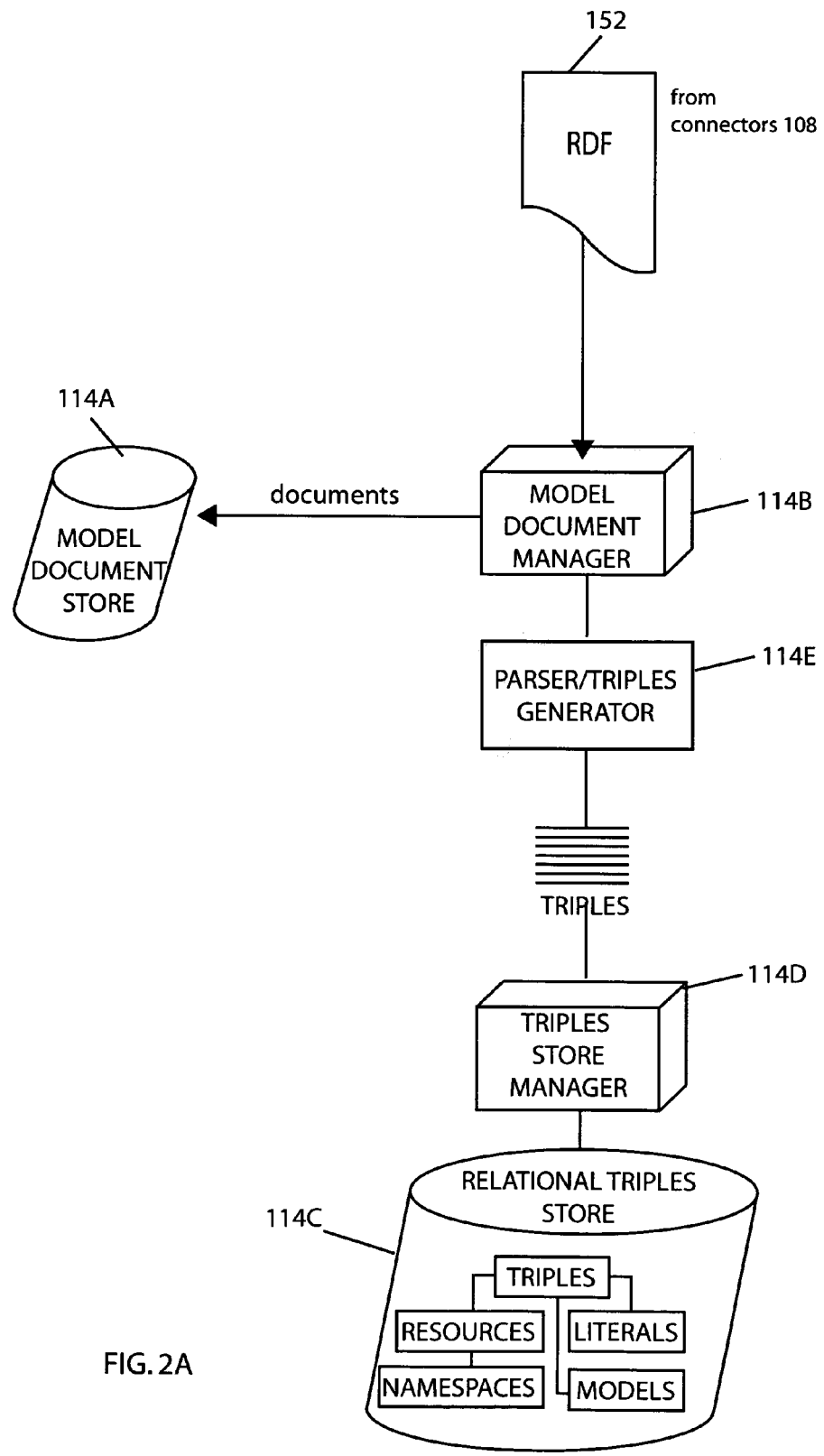
FIG. 2A depicts an architecture for a hologram data store used in the system of FIG. 1.

FIG. 2A depicts an architecture for a preferred hologram data store 114 according to the invention. The illustrated store 114 includes a model document store 114A and a model document manager 114B. It also includes a relational triples store 114C, a relational triples store manager 114D, and a parser 114E interconnected as shown in the drawing.

As indicated in the drawing, RDF triples maintained by the store 114 are received—from the databases 140 (via connectors 108) and/or from time-based data reduction module 150 (described below)—in the form of document objects, e.g., of the type generated from a Document Object Model (DOM) in a JAVA, C++ or other application. In the illustrated embodiment, these are stored in the model document store 114A as such (i.e., document objects) particularly, using the tables and inter-table relationships shown in FIG. 1B (see dashed box labelled 114B).

The model document manager 114B manages storage/retrieval of the document object to/from the model document store 114A. In the illustrated embodiment, the manager 114B comprises the Slide content management and integration framework, publicly available through the Apache Software Foundation. It stores (and retrieves) document objects to (and from) the store 114A in accord with the WebDAV protocol. Those skilled in the art will, of course, appreciate that other applications can be used in place of Slide and that document objects can be stored/retrieved from the store 114A in accord with other protocols, industry-standard, proprietary or otherwise.

However, use of the WebDAV protocol allows for adding, updating and deleting RDF document objects using a variety of WebDAV client tools (e.g., Microsoft Windows Explorer, Microsoft Office, XML Spy or other such tools available from a variety of vendors), in addition to adding, updating and deleting document objects via connectors 108 and/or time-based data reduction module 150. This also allows for presenting the user with a view of a traversable file system, with RDF documents that can be opened directly in XML editing tools or from Java programs supporting WebDAV protocols, or from processes on remote machines via any HTTP protocol on which WebDAV is based.

RDF triples received by the store 114 are also stored to a relational database, here, store 114C, that is managed and accessed by a conventional relational database management system (RDBMS) 114D, operating in accord with the teachings hereof. In that database, the triples are divided into their constituent components (subject, predicate, and object), which are indexed and stored to respective tables in the manner of a "hashed with origin" approach. Whenever an RDF document is added, updated or deleted, a parser 114E extracts its triples and conveys them to the RDBMS 114D with a corresponding indicator that they are to be added, updated or deleted from the relational database. Such a parser 114E operates in the conventional manner known in the art for extracting triples from RDF documents.

Figure 2B:
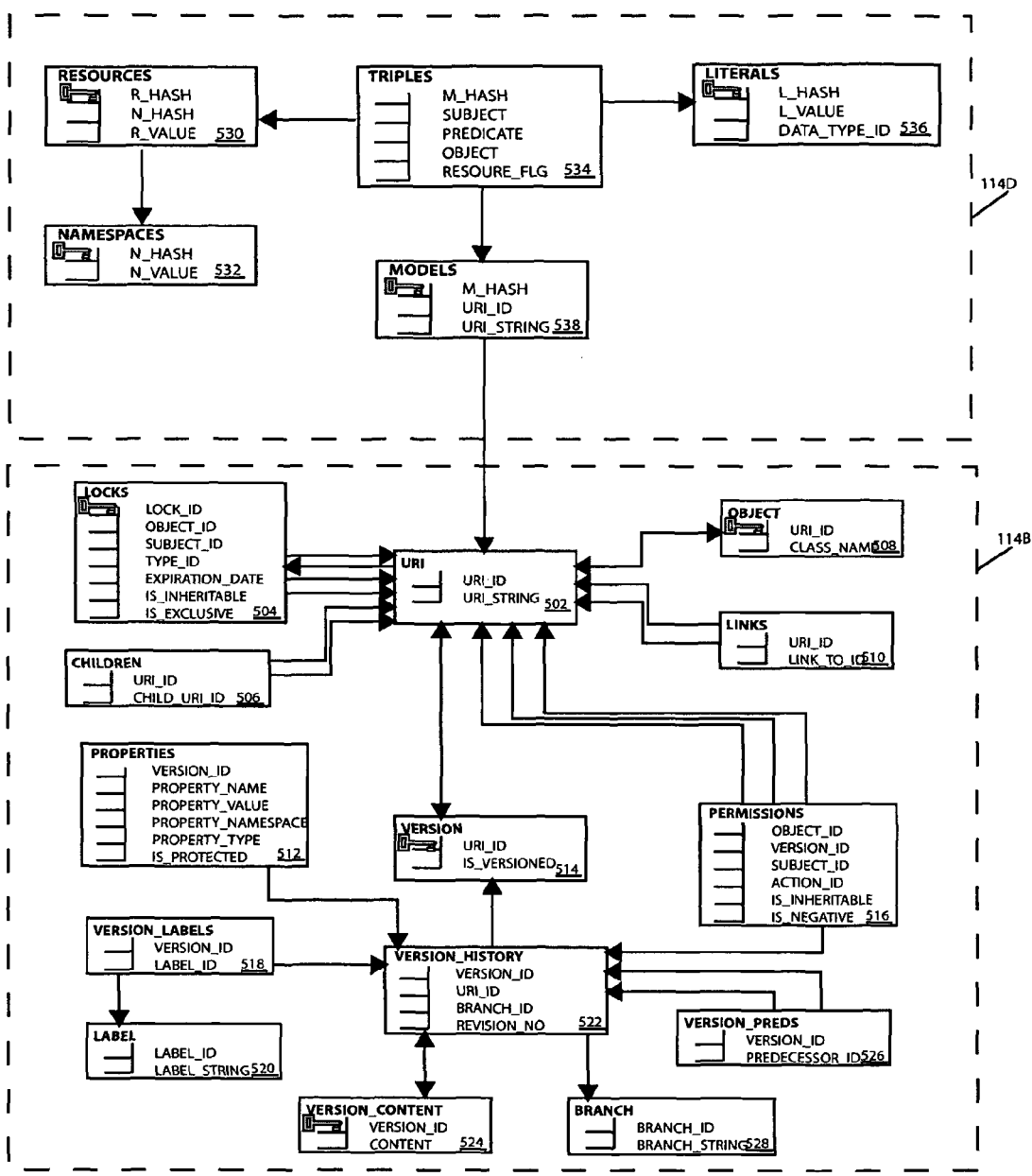
FIG. 2B depicts the tables in a model store and a triples store of the hologram data store of FIG. 2A.

The illustrated database store 114C has five tables interrelated as particularly shown in FIG. 2B (see dashed box labelled 114C). In general, these tables rely on indexes generated by hashing the triples' respective subjects, predicates and objects using a 64-bit hashing algorithm based on cyclical redundancy codes (CRCs)—though, it will be appreciated that the indexes can be generated by other techniques as well, industry-standard, proprietary or otherwise.

Referring to FIG. 2B, the "triples" table 534 maintains one record for each stored triple. Each record contains an aforementioned hash code for each of the subject, predicate and object that make up the respective triple, along with a resource flag ("resource_flg") indicating whether that object is of the resource or literal type. Each record also includes an aforementioned hash code ("m_hash") identifying the document object (stored in model document store 114A) from which the triple was parsed, e.g., by parser 114E.

In the illustrated embodiment, the values of the subjects, predicates and objects are not stored in the triples table. Rather, those values are stored in the resources table 530, namespaces table 532 and literals table 536. Particularly, the resources table 530, in conjunction with the namespaces table 532, stores the subjects, predicates and resource-type objects; whereas, the literals table 536 stores the literal-type objects.

The resources table 530 maintains one record for each unique subject, predicate or resource-type object. Each record contains the value of the resource, along with its aforementioned 64-bit hash. It is the latter on which the table is indexed. To conserve space, portions of those values common to multiple resources (e.g., common <scheme>://<path> identifiers) are stored in the namespaces table 532. Accordingly the field, "r_value," contained in each record of the resources table 530 reflects only the unique portion (e.g., <fragment> identifier) of each resource.

The namespaces table 532 maintains one record for each unique common portion referred to in the prior paragraph (hereinafter, "namespace"). Each record contains the value of that namespace, along with its aforementioned 64-bit hash. As above, it is the latter on which this table is indexed.

The literals table 536 maintains one record for each unique literal-type object. Each record contains the value of the object, along with its aforementioned 64-bit hash. Each record also includes an indicator of the type of that literal (e.g., integer, string, and so forth). Again, it is the latter on which this table is indexed.

The models table 538 maintains one record for each RDF document object contained in the model document store 114A. Each record contains the URI of the corresponding document object ("uri_string"), along with its aforementioned 64-bit hash ("m_hash"). It is the latter on which this table is indexed. To facilitate associating document objects identified in the models table 538 with document objects maintained by the model document store 114A, each record of the models table 538 also contains the ID of the corresponding document object in the store 114A. That ID can be assigned by the model document manager 114B, or otherwise.

From the above, it can be appreciated that the relational triples store 114C is a schema-less structure for storing RDF triples. As suggested by Melnik, an author well known to those skilled in the art of RDF and SQL, triples maintained in that store can be reconstituted via an SQL query. For example, to reconstitute the RDF triple having a subject equal to "postal://zip#02886", a predicate equal to "http://www.metatomix.com/postalCode/1.0#town", and an object equal to "Warwick", the following SQL statement is applied:

```
SELECT m.uri_string, t.resource_flg,
    concat (n1.n_value, r1.r_value) as subj,
    concat (n2.n_value, r2.r_value) as pred,
    concat (n3.n_value, r3.r_value),
    1.1_value
FROM triples t, models m, resources r1, resources r2, namespaces n1, namespaces n2
    LEFT JOIN literals 1 on t.object=1.1_hash
    LEFT JON resources r3 on t.object=r3.r_hash
    LEFT JOIN namespaces n3 on r3.r_value=n3.n_value
```

-continued

```
WHERE   t.subject=r1.r__hash AND r1.n__hash=n1.n__hash AND
        t.predicate=r2.r__hash AND r2.n__hash=n2.n__hash AND
        m.uri__id=t.m__hash AND t.subject=hash("postal://zip#02886") AND
        t.predicate=hash('http://www.metatomix.com/postalcode/1.0#town') AND
        t.object=hash('warwick')
```

Those skilled in the art will, of course, appreciate that RDF documents and, more generally, objects maintained in the store 114 can be contained in other stores—structured relationally, hierarchically or otherwise—as well, in addition to or instead of stores 114A and 114C.

In a system 100 according to the invention used as part of the PHIN network, the maintenance of data in the store 114 is accomplished in a manner compatible with the applicable PHIN standards, e.g., for the use of electronic clinical data for event detection. Thus, for example, data storage is compatible with the applicable logical data model(s), can associate incoming data with appropriate existing data (e.g., a report of a disease in a person who had another condition previously reported), permits potential cases should be "linked" and traceable from detection via electronic sources of clinical data or manual entry of potential case data through confirmation via laboratory result reporting, and permits data to be accessed for reporting, statistical analysis, geographic mapping and automated outbreak detection algorithms, and so forth, all as required under the PHIN standards and further discussed below. Whether maintained in the data store 114, or otherwise, a system 100 according to the invention used as part of the PHIN network, provides directories of public health and clinical personnel accessible as required under the PHIN standards. Systems 100 according to the invention used as part of HAN or NEDSS-compatible networks provide similar functionality, as particularly required under those initiatives.

Referring to FIG. 2A, the relational triples store manager 1 14D supports SQL queries such as the one exemplified above (for extracting a triple with the subject "postal://zip#02886", the predicate "http://www.metatomix.com/postalCode/1.0#town", and the object "Warwick"), in the manner described in commonly assigned U.S. patent application Ser. No. 10/302,764, filed Nov. 21, 2002, entitled METHODS AND APPARATUS FOR QUERYING A RELATIONAL DATA STORE USING SCHEMA-LESS QUERIES, now published as US Patent Application Publication No. 2003/0158841 and PCT WO 03044634 (Application WO2002US0037729), the teachings of which are incorporated herein by reference (see, specifically, for example, FIG. 3 thereof and the accompanying text), and a copy of which may be attached as an appendix hereto (and, if so, as Appendix A).

The data store 114 can likewise include time-wise data reduction component of the type described in commonly assigned U.S. patent application Ser. No. 10/302,727, filed Nov. 21, 2002, entitled METHODS AND APPARATUS FOR STATISTICAL DATA ANALYSIS AND REDUCTION FOR AN ENTERPRISE APPLICATION, now published as US Patent Application Publication No. 2003/0158851 and PCT WO 03046769 (Application W02002US0037727), the teachings of which are incorporated herein by reference (see, specifically, for example, FIG. 3 thereof and the accompanying text), a copy of which may be attached as an appendix hereto (and, if so, as Appendix B), to perform a time-wise reduction on data from the database, streams or other sources 140.

According to one practices of the invention, data store 114 includes a graph generator that uses RDF triples to generate directed graphs in response to queries made—e.g., by a user accessing the store via the browser 118 and server 116, by a surveillance, monitoring and real time events application executing on the server 116 or in connection with the browser 118, by another node on the network 120 and received electronically or otherwise, or made otherwise—for information reflected by triples originating from data in one or more of the databases, streams or other sources 140. Such generation of directed graphs from triples can be accomplished in any conventional manner known the art (e.g., as appropriate to RDF triples or other manner in which the information is stored) or, preferably, in the manner described in co-pending, commonly assigned U.S. patent application Ser. No. 10/138,725, filed May 3, 2002, entitled METHODS AND APPARATUS FOR VISUALIZING RELATIONSHIPS AMONG TRIPLES OF RESOURCE DESCRIPTION FRAMEWORK (RDF) DATA SETS, now published as US Patent Application Publication No. 2003/0208499 and PCT WO 03094142A1 (Application W02003US0012479), and U.S. Patent Application Ser. No. 60/416,616, filed Oct. 7, 2002, entitled METHODS AND APPARATUS FOR IDENTIFYING RELATED NODES IN A DIRECTED GRAPH HAVING NAMED ARCS, now published as PCT WO 04034625 (Application W02003US0031636) and issued as U.S. Pat. No. 6,954,749, a copy of which may be attached as an appendix hereto (and, if so, as Appendix C), the teachings of both of which are incorporated herein by reference. Directed graphs so generated can be passed back to the server 116 for presentation to the user via browser 118, they can be "walked" by the server 116 to identify specific information responsive to queries, or otherwise.

Alternatively, or in addition, to the graph generator, the data store 114 can utilize genetic, self-adapting, algorithms to traverse the RDF triples in response to such queries. To this end, the data store utilizes a genetic algorithm that performs several searches, each utilizing a different methodology but all based on the underlying query from the framework server, against the RDF triples. It compares the results of the searches quantitatively to discern which produce(s) the best results and reapplies that search with additional terms or further granularity.

Figure 3:
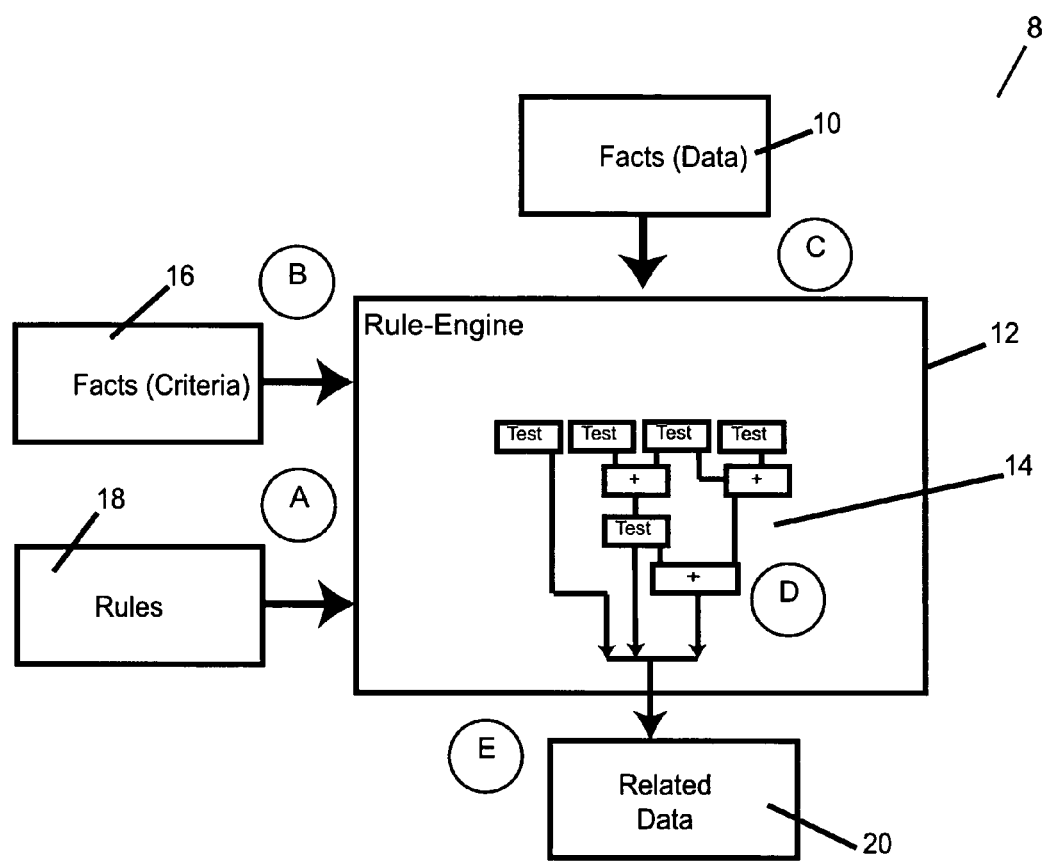
FIG. 3 depicts an expert engine to identify information in the data store or from the other information in the system of FIG. 1.

In some practices of the invention, surveillance, monitoring and real-time events applications executing on the connectors 108, the server 116, the browser and/or the data store 114 utilize an expert engine-based system 8 of the type shown in FIG. 3 to identify information in the data store 114 and/or from sources 140 responsive to queries and/or otherwise for presentation via browser 118, e.g., in the form of alerts, reports, or otherwise. The information so identified can, instead or in addition, form the basis of further processing, e.g., by such surveillance, monitoring and real-time events applications, in the form of broadcasts or messages to other nodes in the network 120, or otherwise, consistent with requirements of PHIN, HAN or other applicable standards.

Thus, for example, in a system 100 adapted for use in a node on the PHIN, the system 8 can be used to process data incoming from the sources 140 to determine whether it should be ignored, stored, logged for alert or classified otherwise. Data reaching a certain classification limit, moreover, can be displayed via the browser 118 and, more particularly, the dashboard discussed below, e.g., along with a map of the state, country or other relevant geographic region and/or along with other similar data.

Alternatively, in a system 100 adapted for use in a NEDSS compliant node, the expert engine-based system 8 can be used to detect the numbers of instances occurring over time and, if the number exceeds a threshold, to generate a report, e.g., for display via a dashboard window, or generate alert messages for transfer over the network 120 to targeted personnel (e.g., as identified by action of further rules or otherwise). In such a system 100, the expert engine can also be used to subset data used for display or reporting in connection with the collaborative function, e.g., specified under the CDC's HAN guidelines.

Referring to FIG. 3, the system 8 includes a module 12 that executes a set of rules 18 with respect to a set of facts 16 representing criteria in order to (i) generate a subset 20 of a set of facts 10 representing an input data set, (ii) trigger a further rule, and/or (iii) generate an alert, broadcast, message, or otherwise. For simplicity, in the discussion that follows the set of facts 16 representing criteria are referred to as "criteria" or "criteria 16," while the set of facts 10 representing data are referred to as "data" or "data 10."

Illustrated module 12 is an executable program (compiled, interpreted or otherwise) embodying the rules 18 and operating in the manner described herein for identifying subsets of directed graphs. In the illustrated embodiment, module 12 is implemented in Jess (Java Expert System Shell), a rule-based expert system shell, commercially available from Sandia National Laboratories. However it can be implemented using any other "expert system" engine, if-then-else network, or other software, firmware and/or hardware environment (whether or not expert system-based) suitable for adaptation in accord with the teachings hereof.

The module 12 embodies the rules 18 in a network representation 14, e.g., an if-then-else network, or the like, native to the Jess environment. The network nodes are preferably executed so as to effect substantially parallel operation of the rules 18, though they can be executed so as to effect serial and/or iterative operation as well or in addition. In other embodiments, the rules are represented in accord with the specifics of the corresponding engine, if-then-else network, or other software, firmware and/or hardware environment on which the embodiment is implemented. These likewise preferably effect parallel execution of the rules 18, though they may effect serial or iterative execution instead or in addition.

The data set 10 can comprise any directed graph, e.g., a collection of nodes representing data and directed arcs connecting nodes to one another, though in the illustrated embodiment it comprises RDF triples contained in the data store 114 and/or generated from information received from the sources 140 via connectors 108. Alternatively, or in addition, the data set can comprise data structures representing a meta directed graph of the type disclosed in co-pending, commonly assigned U.S. patent application Ser. No. 10/138,725, filed May 3, 2002, entitled METHODS AND APPARATUS FOR VISUALIZING RELATIONSHIPS AMONG TRIPLES OF RESOURCE DESCRIPTION FRAMEWORK (RDF) DATA SETS, e.g., at FIG. 4A-6B and accompanying text, all of which incorporated herein by reference.

Criteria 16 contains expressions including, for example, literals, wildcards, Boolean operators and so forth, against which nodes in the data set are tested. In embodiments that operate on RDF data sets, the criteria can specify subject, predicate and/or object values or other attributes. In embodiments that operate on directed graphs of other types other appropriate values and attributes may be specified. The criteria can be input by a user, e.g., via browser 118, e.g., on an ad hoc basis. Alternatively or in addition, they can be generated by surveillance, monitoring and real-time events applications executing on the connectors 108, the server 116, the browser and/or the data store 114.

Rules 18 define the tests for identifying data in the data set 20 that match the criteria or, where applicable, are related thereto. These are expressed in terms of the types and values of the data items as well as their interrelationships or connectedness. By way of example, a set of rules applicable to a data set comprised of RDF triples for identifying triples that match or are related to the criteria are disclosed in aforementioned incorporated by reference U.S. patent application Ser. No. 60/416,616, filed Oct. 7, 2002, entitled METHODS AND APPARATUS FOR IDENTIFYING RELATED NODES IN A DIRECTED GRAPH HAVING NAMED ARCS, now issued as U.S. Pat. No. 6,954,749 (see, Appendix C hereof). Those skilled in the art will, of course, appreciate that different rules may be applicable depending on the nature and focus of the information sought by any given surveillance, monitoring and real-time events application and that construction of such rules is within the ken of those skilled in the art based on the teachings hereof.

Referring to back to FIG. 3, the data 20 output or otherwise generated by module 12 represents those triples matching (or, where applicable, related) to the criteria as determined by exercise of the rules. The data 20 can be output as triples or some alternate form, e.g., pointers or other references to identified data within the data set 10, depending on the needs of the surveillance, monitoring and real-time events application that invoked the system 8. As noted above, instead of or in addition to outputting data 20, the module 12 triggers execution of further rules, generate alerts, broadcasts, messages, or otherwise, consistent with requirements of PHIN, HAN or other applicable standards.

The framework server 116 presents information from the data store 114 and/or sources 140 via browser 118. This can be based on requests entered directly by the user directly, e.g., in response to selections/responses to questions, dialog boxes or other user-input controls generated by a surveillance, monitoring and real-time events application executing on the server 116 or in connection with the browser 118. It can also be based, for example, on information obtained from the database 114 and/or sources 140 by the expert engine-based system 8 described above.

A further understanding of the operation of the framework server 116 may be attained by reference to the appendix filed with U.S. patent application Ser. No. 09/917,264, filed Jul. 27, 2001, now published as US Patent Application Publication No. 2002/0178170 and PCT WO02093319A2 and EP 1405219A2 (Application EP2002000741711), and entitled METHODS AND APPARATUS FOR ENTERPRISE APPLICATION INTEGRATION, which appendix is incorporated herein by reference.

According to one practice of the invention, a surveillance, monitoring and real-time events application includes a "dashboard" with display windows or panels that provide comprehensive real-time displays of information gathered from the data store 114 or other sources 140, as well as "alerts" resulting from anomalous situations detected by the surveillance, monitoring and real-time events application. The dashboard and alerts can be generated by an application executing on the server 116 and/or the browser 118 or otherwise.

Surveillance, monitoring and real-time events dashboards can display information and alerts that are specific to predefined categories, such as boarder and port security, health and bioterrorism, or public and community safety. These can be configured by users to display information from ad hoc combinations of data sources and user-defined alerts. For the purpose of describing the structure and operation of the surveillance, monitoring and real-time events dashboards, reference will be made to two representative examples (boarder/port security and health/bioterrorism), although these descriptions apply to other predefined and user-defined categories of information.

Figure 4:
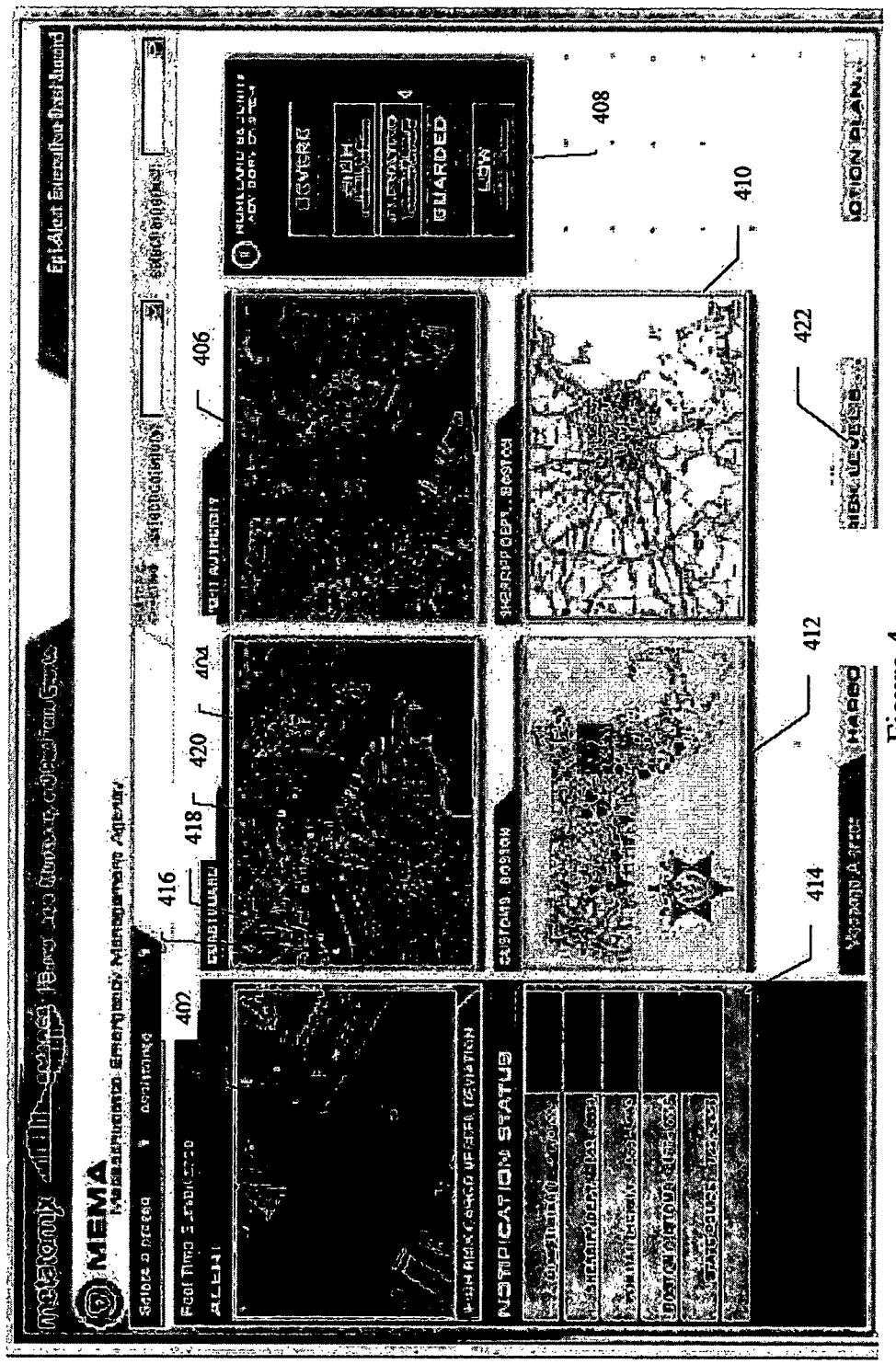

FIG. 4 illustrates a border/port security dashboard 400. The dashboard displays several panels 402, 404, 406, 408, 410, 412 and 414. Panel 402 can be used to display information relating to an alert, if one has been issued by the surveillance, monitoring and real-time events application or by an external system. Panel 402 is described in more detail below. Each panel 404-414 displays information from a particular data source or an aggregation of data from several data sources. For example, panel 404 can contain real-time radar data from the US Coast Guard superimposed on a satellite image of Boston's inner harbor. The panel 404 display can be augmented with other Coast Guard data. For example, global positioning system (GPS) data from US Coast Guard vessels and vehicles (collectively "units") can be used to identify and then look up information related to these units. The unit identities can be superimposed on the image displayed in panel 404, as shown at 416, 418 and 420. Double-clicking on one of these units can cause the surveillance, monitoring and real-time events application to display information about the unit. This information can include, for example, contact information (e.g. frequency, call sign, name of person in charge, etc.), capabilities (e.g. maximum speed, crew size, weaponry, fire-fighting equipment, etc.) and status (e.g. docked, patrolling, busy intercepting a vessel, etc.).

Panel 406 can contain real-time data from a port authority superimposed on a map of the inner harbor. Note that port authority data can include information related to the inner harbor that is different than information provided by the US Coast Guard. For example, the port authority data can include information on vessels traveling or docked within the inner harbor. Furthermore, the port authority data can relate to more than just the inner harbor. For example, the port authority data can include information related to an airport and a rail yard.

Other panels 410 and 412 can display information from other data sources, such as US Customs and local or state police. Panel 408 displays a current Homeland Security Advisory System threat level. Panel 414 displays contact information for agencies, such as the US Coast Guard, US Customs, port authority and state police, that might be invoked in case of an alert.

Figure 5:
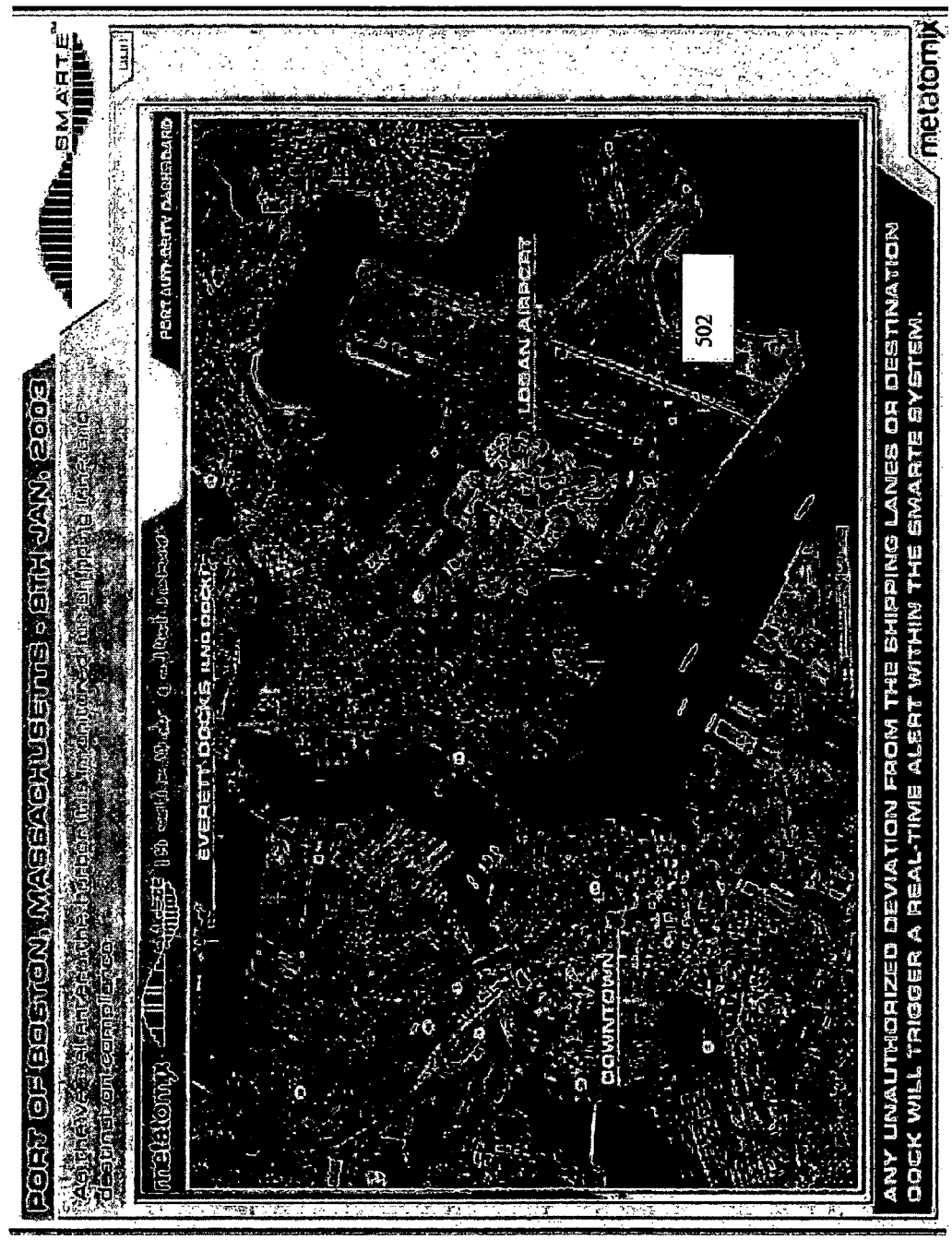
Figure 6:

A user can double-click on any panel to display a separate window containing the panel. By this mechanism, the user can enlarge any panel. In addition, through appropriate mouse or keyboard commands, the user can zoom in on a portion of the image displayed by a panel. For example, the user can select a point on the panel display to re-center the display to the selected point and zoom in on that point. Alternatively, the user can select a rectangular portion of the panel display using a "rubber band" cursor and instruct the system to fill the entire panel with the selected portion. FIG. 5 illustrates an example of such a window 500 displaying the port authority panel 406 of FIG. 4. A user can, for example, double-click on a vessel 502 to display information about the vessel. FIG. 6 illustrates an example of a pop-up window 600 that displays information about the selected vessel.

Although panels 402-414 contain graphical displays, other panels (not shown) can contain textural or numeric data. For example, panels containing shipping schedules, airline schedules, port volume statistics, recent headlines, weather forecasts, etc. can be available for display. Of course, other graphical panels, such as current meteorological data for various portions of the world, can also be available. The surveillance, monitoring and real-time events application can make available more panels than can be displayed at one time on the dashboard 400 (FIG. 4). The dashboard 400 can display a default set of panels, such as panels 404-414. Optionally, the user can select which panels to display in the dashboard 400, as well as arrange the panels within the dashboard and control the size of each panel. If it is deemed desirable to display more panels than can be displayed at one time, some or all of the desired panels can be displayed on a round-robin basis.

In addition to allowing users to select items on panels to obtain further information about these items, the surveillance, monitoring and real-time events application can include rules and/or heuristics to automatically detect anomalies and alert users to these anomalies (hereinafter referred to as "alerts"). As a result of one of these alerts, the surveillance, monitoring and real-time events application preferably can select one or more panels containing particularly relevant information and display or enlarge those panels. The selected panels need not be ones that the user could select. For example, the surveillance, monitoring and real-time events application can create a new panel that, includes a combination of data from several sources, the sources being selected by rule(s) that caused the alert to be issued.

Figure 7:
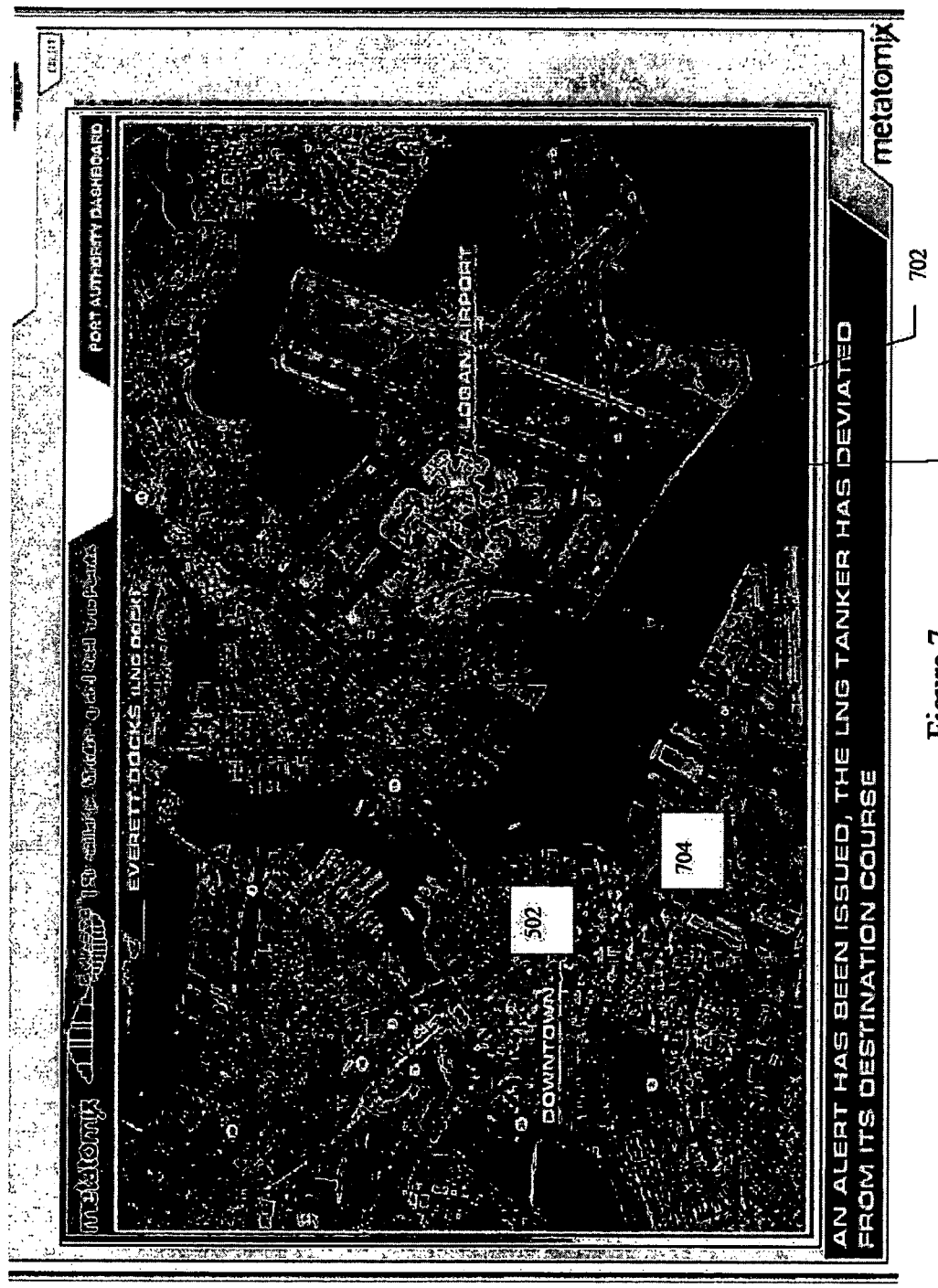

The following example illustrates how an alert can be issued. As shown in FIG. 7, the inner harbor can be partitioned into shipping lanes 700 and 702. The surveillance, monitoring and real-time events application can include rules describing permitted, required and/or prohibited behavior of vessels in these shipping lanes 700 and 702. Some rules can apply to all vessels. Other rules can apply to only certain vessels, for example according to the vessels' types, cargos, speeds, country of registry, as well as according to data unrelated to the vessels, such as time of day, day of week, season, Homeland Security Advisory System threat level, amount of other harbor traffic or amount or schedule of non-harbor traffic, such as aircraft at an adjacent airport. Other rules can apply to docked vessels, vessels under tow, etc. Similarly, rules can apply to aircraft, vehicles, or any measurable quantity, such as air quality in a subway station, seismic data, voltage in a portion of a power grid or vibration in a building, bridge or other structure. Rules can also apply to data entered by humans, such as the number of reported cases of food poisoning or quantities of antibiotics prescribed, ordered or on hand during a selected period of time.

Under normal circumstances, i.e. when no alerts are pending, the dashboard 400 (FIG. 4) displays a default set of panels or a set of panels selected by the user, as previously described. If, for example, the previously mentioned tanker vessel 502 (FIG. 7) carrying a hazardous cargo, such as liquefied natural gas (LNG), deviates 704 from a prescribed course, the surveillance, monitoring and real-time events application can issue an alert. Note that rules for vessels carrying hazardous cargos can be different than for vessels carrying non-hazardous cargos. In addition, other vessels can trigger the alert. For example, if the LNG tanker 502 is traveling within its prescribed course, but a high-speed vessel (not shown) or an aircraft is on a collision course with the LNG tanker, the surveillance, monitoring and real-time events application can issue an alert.

As a result of the alert, the surveillance, monitoring and real-time events application displays the alert panel 402 (FIG. 4) and an alert message 422. In this case, the alert panel 402 displays a zoomed-in portion of the port authority panel 406. In addition, the surveillance, monitoring and real-time events application can automatically notify a predetermined list of people or agencies. The particular people or agencies can depend on factors, such as the time of day or the day of the week of the alert. Optionally, the surveillance, monitoring and real-time events application can notify other users at other nodes, such as nodes 100b, 100c, 100d and/or 100e (FIG. 1). Information displayed on dashboards (not shown) at these other nodes 100b-e need not be the same as information displayed on the dashboard 400. In particular, the information displayed on these other nodes 100b-e can be more or less detailed than the information displayed on the dashboard 400. For example, summary information, such as an icon displayed on a map of the United States, can be displayed at command/control node to indicate an alert in Boston, without necessarily displaying all details related to the alert. A user at the command/control node can double-click on the icon to obtain more detailed information.

Figure 8:
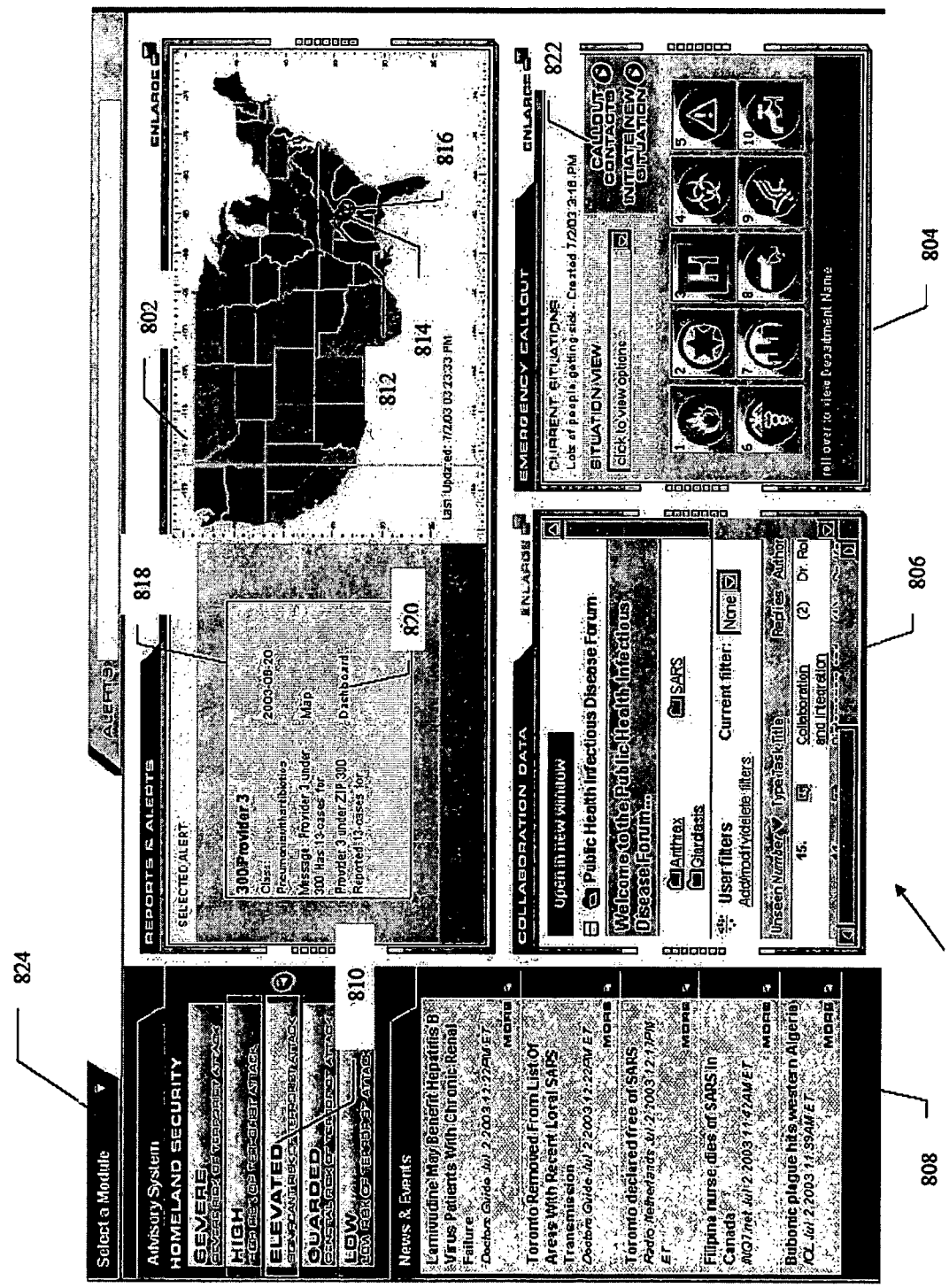

FIGS. 8-16 illustrate an exemplary dashboard that can be used in a health and bioterrorism context. FIG. 8 illustrates a dashboard 800 that contains several panels 802, 804, 806, 808 and 810. Panel 802 contains a map of the United States with icons 812, 814, 816 indicating locations of three alerts. Panel 804 contains emergency contact information that is relevant to the alerts. Panel 806 contains hyperlinks to discussion forums, in which agency representatives and other authorized groups and people can post messages and replies, as is well known in the art. Panel 808 contains hyperlinks to information that is relevant to the alerts. Panel 810 displays the current Homeland Security Advisory System threat level. These panels will be described in more detail below.

Figure 9:
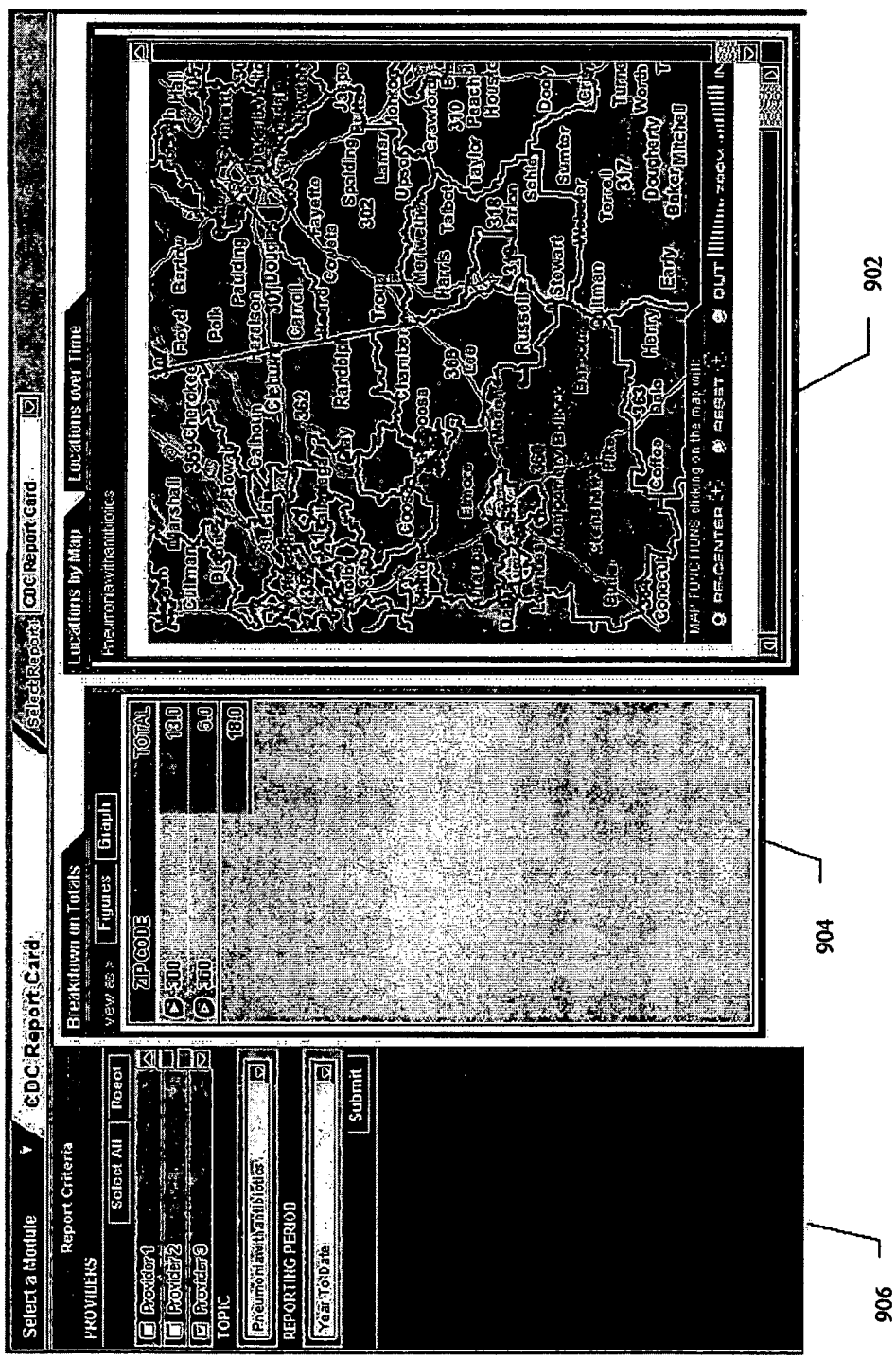

In this example, the icons 812, 814 and 816 represent medical care providers that have experienced noteworthy events or levels of activity. As previously described, an alert can be issued if, for example, the number of cases of disease, such as influenza, exceeds a predetermined threshold. In this example, Provider 3 has encountered patients with pneumonia that does not respond to antibiotics. The other alerts could relate to other anomalous events or levels of activity. Clicking the icon 816 causes the system to display information 818 related to the selected alert. Clicking on a link 820 causes the system to display more detailed information about the alert. For example, FIG. 9 illustrates two panels 902 and 904, as well as a user selection area 906, that can be displayed. Panel 902 contains a more detailed map of the area in which the event occurred. Panel 904 list the number of cases by zip code of the patients. User selection area 906 enables the user to select one or more of the alerts, thereby selecting or aggregating data from the selected provider(s) for display in panels 902 and 904.

Figure 10:
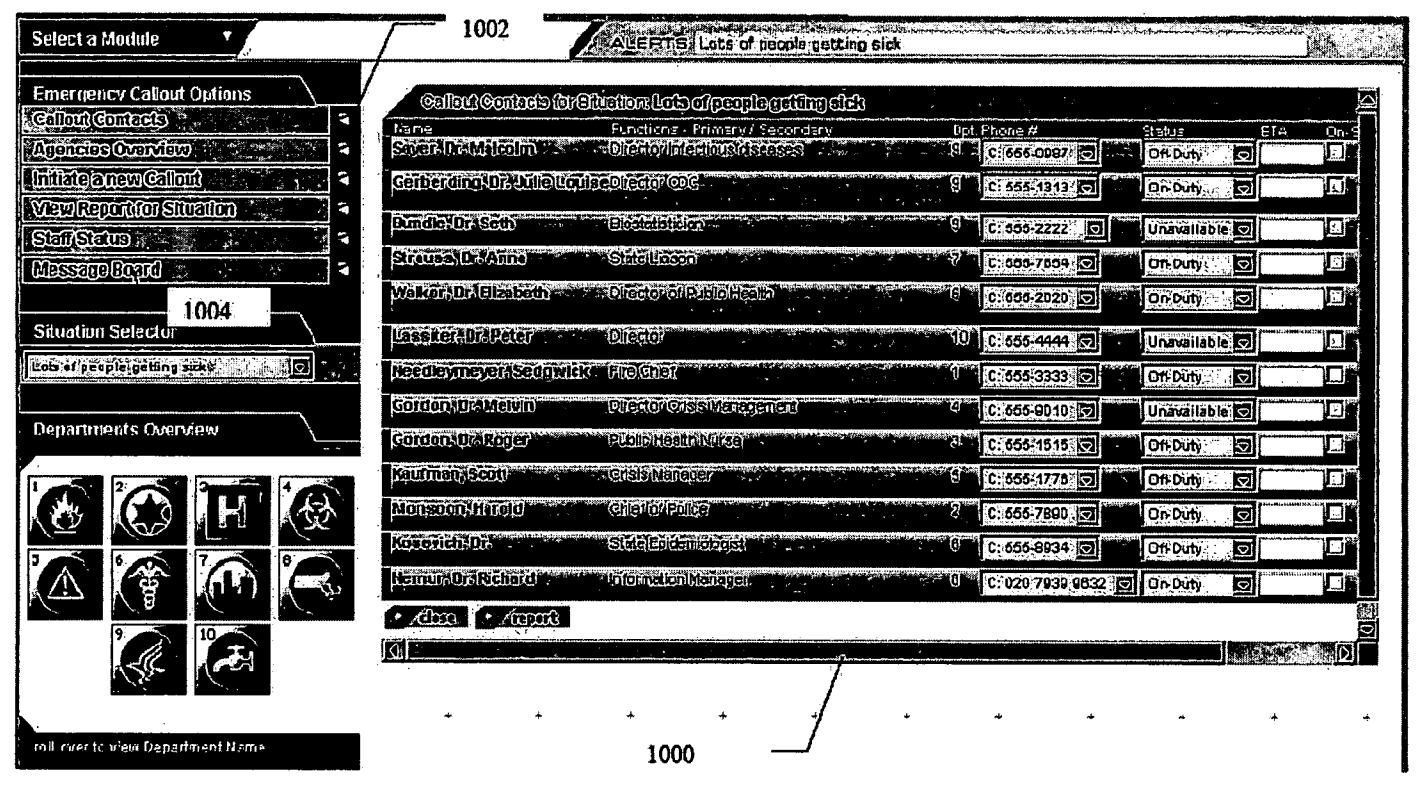
Figure 11:
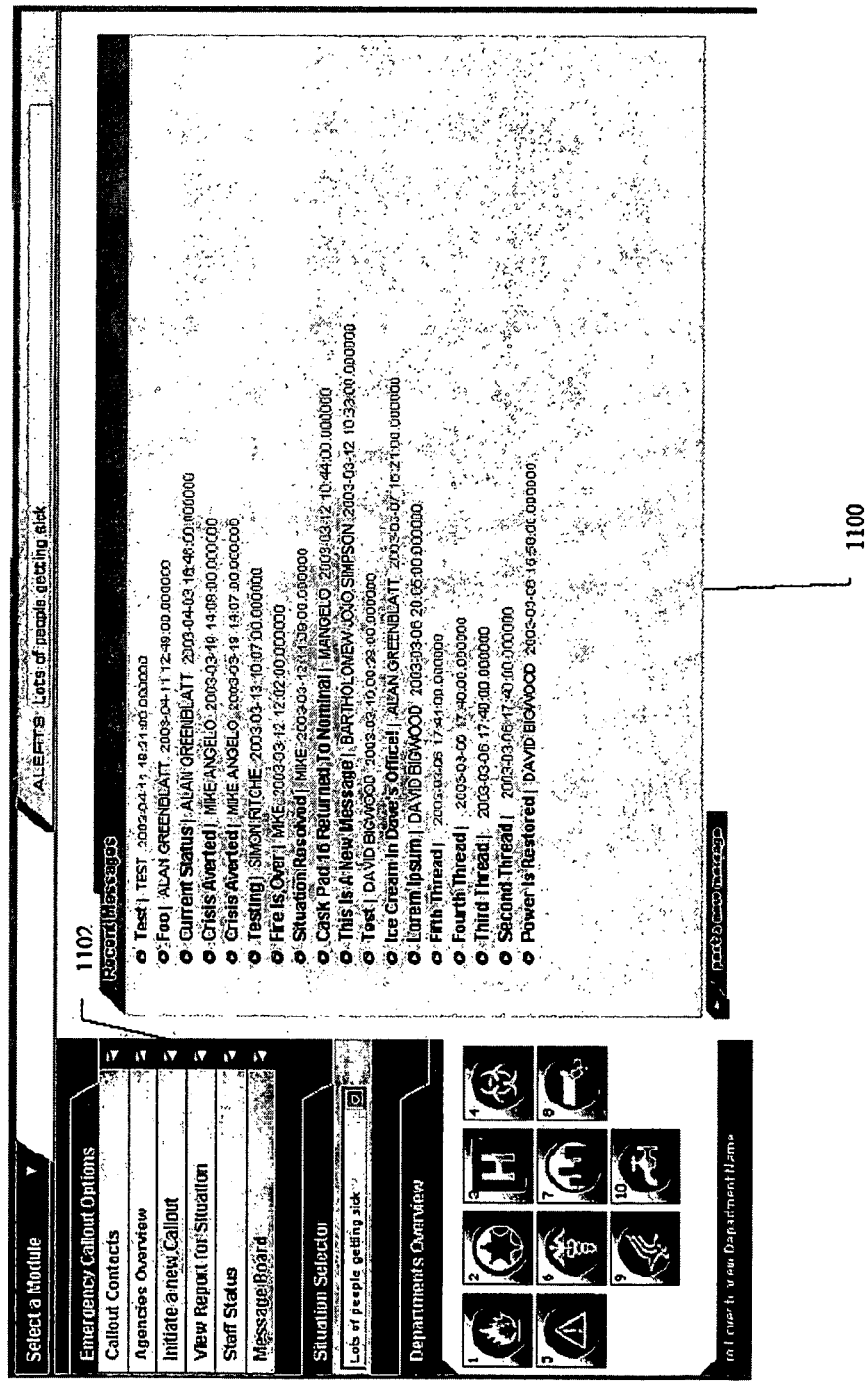
Figure 12:
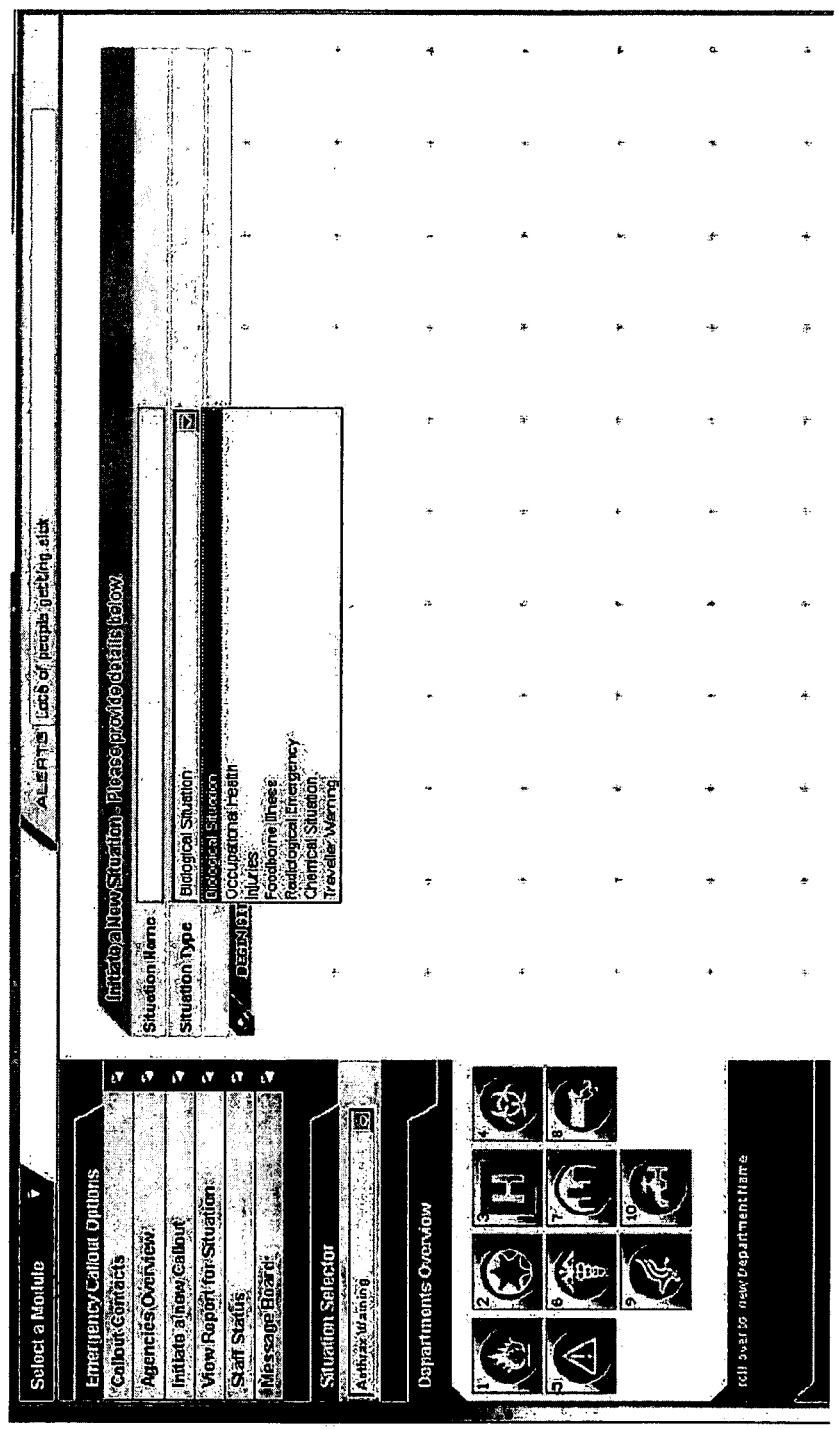

Returning for a moment to FIG. 8, panel 804 contains icons for government agencies and other individuals or organizations (collectively "responders") that might be called upon to respond to manage a biological, nuclear, foodborne or other situations identified by the expert engine-based system 8 (e.g., as where the number of instances matching a specified criteron exceeds a threshold). Clicking link 822 displays a window containing emergency contact information for these responders, as shown in FIG. 10 at 1000. Panel 1002 contains several emergency callout options, by which the user can manage the alerts. For example, clicking "Message Board" link 1004 displays a window containing messages posted in relation to this alert, as shown in FIG. 11 at 1100. This message board enables users and responders to communicate with each other in relation to the alert. An "Initiate a new Callout" link 1102 enables the user to initiate a new situation, as shown in FIG. 12.

Figure 13:
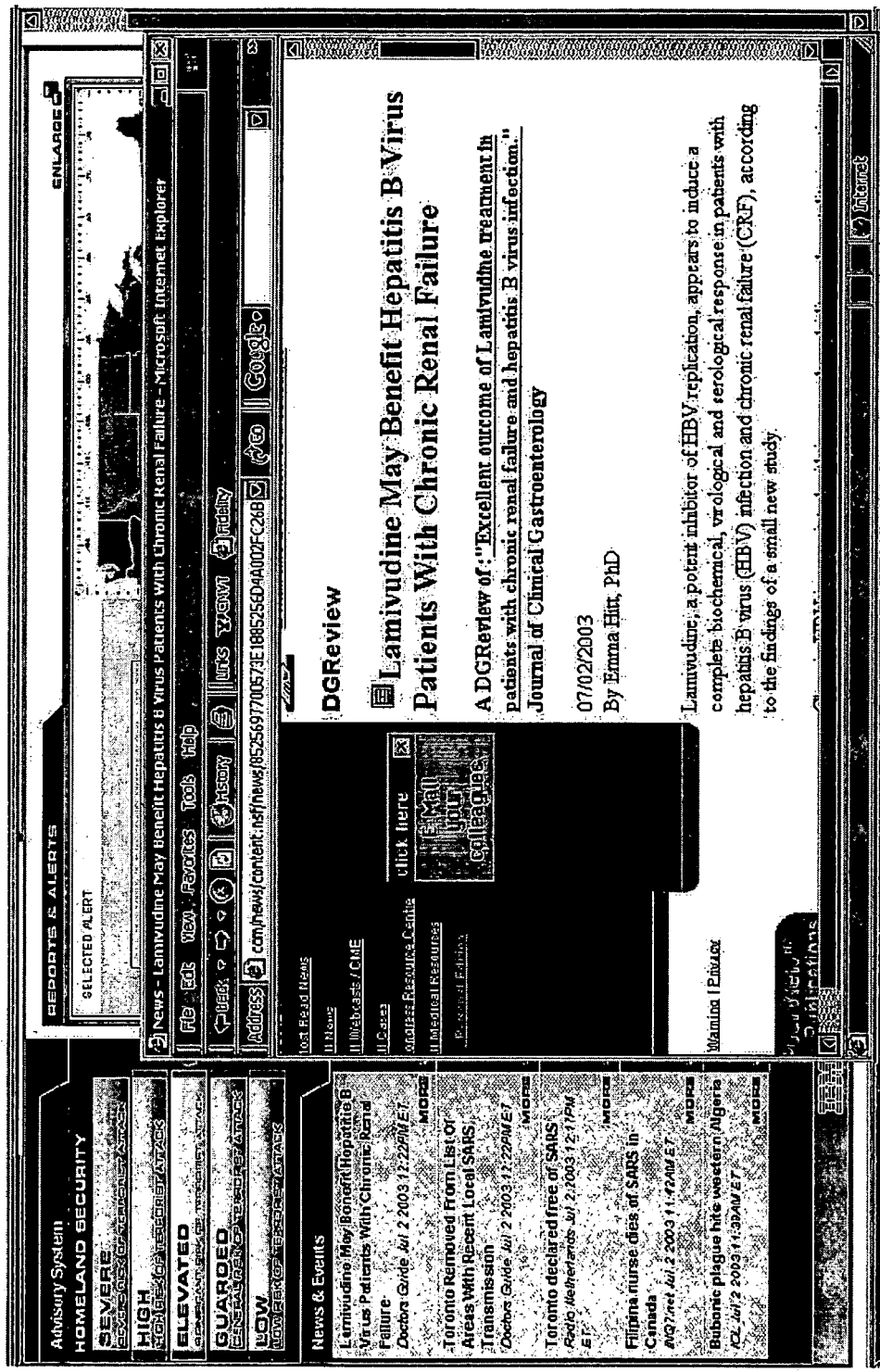

In response to an alert, the surveillance, monitoring and real-time events application automatically performs searches of the Internet and responder intranets for information relevant to the alert. As previously mentioned, panel 808 (FIG. 8) contains hyperlinks to information that is relevant to the alerts, including results from these searches and predefined information sources that have been identified as relevant. The surveillance, monitoring and real-time events application can, for example, have a database of information sources catalogued according to alert type. As shown in FIG. 13, clicking on one of the hyperlinks in the panel 808 opens a new window 1300 displaying contents identified by the hyperlink.

Returning again to the dashboard 800 shown in FIG. 8, the user can select a module via a pull-down list 824. For example, the user can select "Reports", in which case the system displays a window similar to that shown in FIG. 14. After selecting one or more providers 1402 and 1404, the system displays a report in a report panel 1406.

Figure 15:
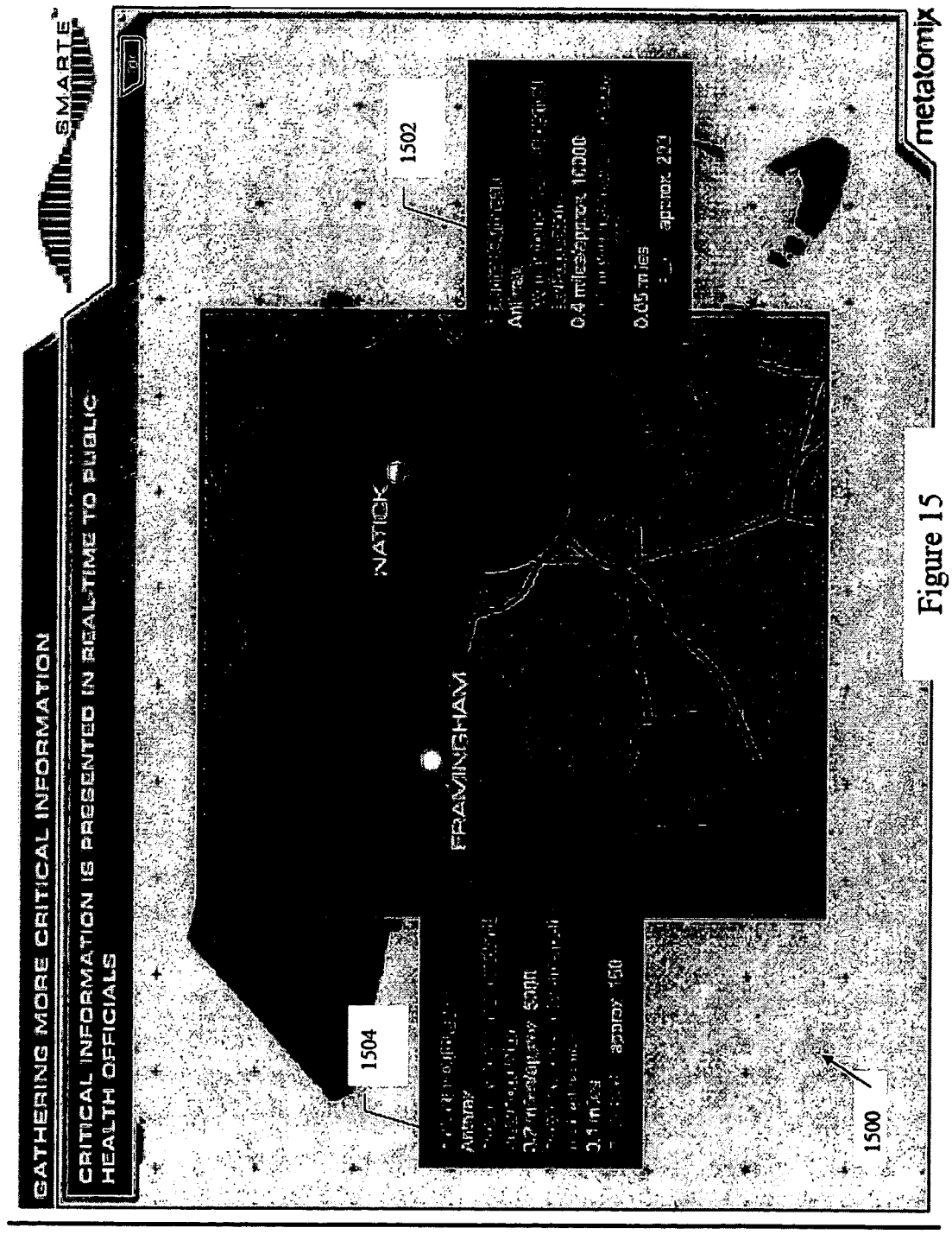
Figure 16:
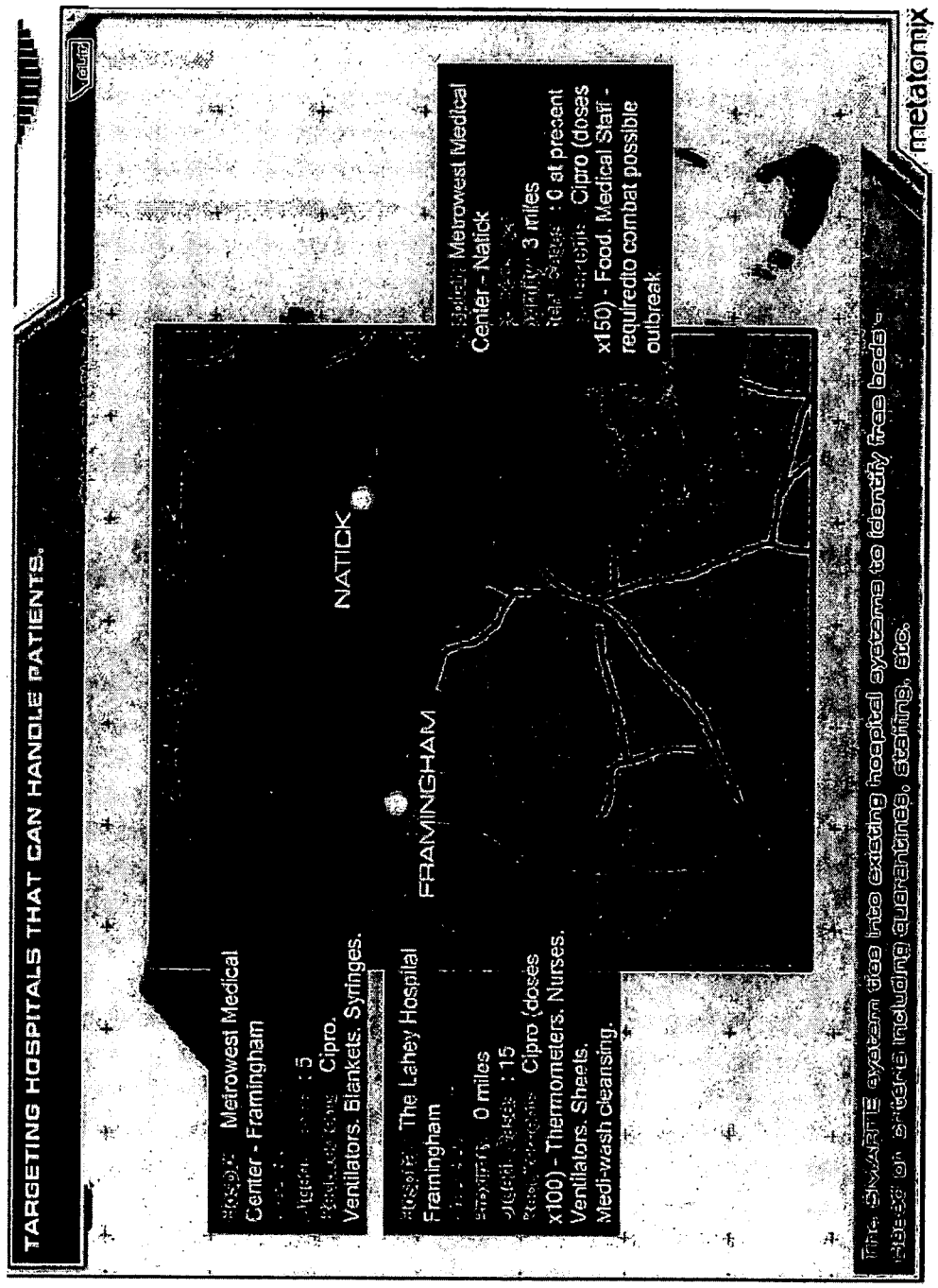

FIG. 15 illustrates another graphical display 1500, by which the system can display an alert. In the example of FIG. 15, two potential outbreaks of anthrax are shown. For each potential outbreak, the system displays information, such as proximity of the outbreak to the nearest residential area, as well as the population of the residential area, proximity to the nearest emergency medical center and the number of free beds in the medical center. Being tied into existing hospital systems, the surveillance, monitoring and real-time events application can query those hospital systems and display relevant information, as shown in FIG. 16.

Described herein are methods and apparatus meeting the above-mentioned objects. It will be appreciated that the illustrated embodiment is merely an example of the invention and that other embodiments, incorporating changes to those described herein, fall within the scope of the invention. Thus, for example, as noted earlier, although the illustrated embodiment is adapted for use in public health & bioterrorism application (with additional examples provided with respect to border and port security) it will be appreciated that a similar such systems can be applied in public & community safety, and government data integration applications, described above, among others.

The invention claimed is:
1. A digital data processing system comprising:
query functionality to (i) apply requests to a plurality of data sources using an application program interface ("API") associated with each of the data sources, wherein at least two of the plurality of data sources utilize different APIs, (ii) receive data from the plurality of data sources in response to the requests and to route that data to a data store,
the data store to store the data from the plurality of data sources in the form of resource description framework (RDF) triples, where, in a directed graph representation, one or more of the triples are related to one or more others of the triples by any of an ancestor and a descendant relationship,
an expert engine, coupled to at least one member of a group consisting of (i) the plurality of data sources and the query functionality, to execute rules that operate on the RDF triples to identify related data in the data store, the related data including data that match specified criteria or are related thereto, wherein the expert engine is configured to execute the rules to any of (a) trigger further execution of rules and (b) generate alerts; and a framework module, coupled to the expert engine, to provide data to allow display by one or more displays of information from the data store, as well as one or more alerts resulting from anomalous situations with respect thereto;

wherein the system is configured to perform one or more searches of the plurality of data sources to identify information relevant to the one or more alerts and wherein the data provided by the framework module allows display of the results of at least one member of a group consisting of the one or more searches and links to the results.

2. The digital data processing system of claim 1, wherein the rules executed by the expert engine include rules to:
(i) identify, as related, data substantially matching a criteria, and
(ii) identify, as related, data that is a direct ancestor of data identified in any of (i) and (ii), and that is not in substantial conflict with the criteria.

3. The digital data processing system of claim 1, wherein the data provided by the framework module configures a dashboard to provide one or more real-time displays of information from the data store.

4. The digital data processing system of claim 1, wherein the data provided by the framework module allows display of a plurality of panels as a result of the one or more alerts.

5. The digital data processing system of claim 2, wherein the one or more real-time displays comprise a plurality of panels, and, as a result of the one or more alerts, the framework module provides data to a dashboard to allow at least one member of a group consisting of (i) selection of one or more of the panels and (ii) creation of another panel that includes data from two or more of the plurality of data sources.

6. The digital data processing system of claim 3, wherein the one or more real-time displays comprise a plurality of panels, and, as a result of the one or more alerts, the framework module provides data to a dashboard to allow at least one member of a group consisting of (i) selection of one or more of the panels and (ii) creation of another panel that includes data from two or more of the plurality of data sources, the two or more data sources being selected based on at least one member of a group consisting of (i) a rule and (ii) a heuristic that caused the one or more alerts to be issued.

7. The digital data processing system of claim 1, wherein the plurality of data sources comprise network nodes at one or more clinical care providers, laboratories, governmental health departments, centers for disease control, and law enforcement offices.

8. The digital data processing system of claim 1, wherein the query functionality comprises any of a graph generator, algorithmic search, and an expert engine.

9. The digital data processing system of claim 1, wherein the plurality of data sources are compliant with a public health information network (PHIN) protocol, a health area network (HAN) protocol, National Electronic Disease Surveillance System (NEDSS) protocol, or other protocol for communication of at least one member of a group consisting of: (i) health and (ii) bioterrorism data and wherein the query functionality applies requests to, and receives information from, one or more of the plurality of data sources utilizing an API or interface mechanism dictated by the PHIN, HAN or NEDSS or other protocol communication of information used in communication of health and bioterrorism data.

10. The digital data processing system of claim 9, wherein the query functionality applies SQL queries to selected ones of the plurality of data sources.

11. The digital data processing system of claim 2, wherein the criteria specifies a named relationship and a characteristic of that named relationship, and wherein to identify, as related, includes to compare at least one of the relationship and the characteristic named in a criteria with any of
(a) attributes of the direct ancestor, and
(b) a relationship between the direct ancestor and any data that descends therefrom, in order to determine whether the director ancestor is in substantial conflict with the criteria.

12. The digital data processing system of claim 1, wherein the framework module generates data to allow display of a border/port security display comprising a plurality of panels, a first of which displays information relating to at least one of the one or more alerts, a second of which displays information from a particular data source or an aggregation of data from several data sources, a third of which displays real-time data from a data source superimposed on a map of a locale.

13. The digital data processing system of claim 11, wherein the framework module generates data to allow a dashboard to respond to a selected user input with respect to an item displayed in one of the panels by displaying additional information about that item.

14. The digital data processing system of claim 12, wherein the framework module generates data to allow a dashboard to respond to an alert by displaying a zoomed-in portion of a locale shown in one of the panels and wherein the system includes additional functionality for alerting people, agencies or other entities of such alert.

15. The digital data processing system of claim 1, configured for any of border & port security, public & community safety, and government data integration applications.

16. A digital data processing system comprising:
query functionality to (i) apply requests to a plurality of data sources using an application program interface ("API") associated with each of the data sources, wherein at least two of the plurality of data sources utilize different APIs, (ii) receive data from the plurality of data sources in response to the requests and to route that data to a data store, the data store to store the data from the plurality of data sources in the form of resource description framework (RDF) triples, where, in a directed graph representation, one or more of the triples are related to one or more others of the triples by any of an ancestor and a descendant relationship, an expert engine, coupled to at least member of a group consisting of (i) the plurality of data sources and the query functionality, to execute rules that operate on the RDF triples to identify related data in the data store, the related data including data that match specified criteria or are related thereto, wherein the rules executed by the expert engine include rules to:
(i) identify, as related, data substantially matching a criteria, and
(ii) identify, as related, data that is a direct ancestor of data identified in any of (i) and (ii), and that is not in substantial conflict with the criteria, wherein the expert engine is configured to execute the rules to any of (a) trigger further execution of rules and (b) generate alerts; and, a framework module, coupled to the expert engine, to provide data to allow display by one or more displays of information from the data store, as well as one or more alerts resulting from anomalous situations with respect thereto.

17. The digital data processing system of claim 16, wherein the system is configured to perform one or more searches of the plurality of data sources to identify information relevant to the one or more alerts and provide data to display the results of at least one member of a groups consisting of: (i) the one or more searches and (ii) links to those results.

18. The digital data processing system of claim 16, wherein the data provided by the framework module configures a dashboard to provide one or more real-time displays of information from the data store.

19. The digital data processing system of claim 16, wherein the data provided by the framework module allows display of a plurality of panels as a result of the one or more alerts.

20. The digital data processing system of claim 18, wherein the one or more real-time displays comprise a plurality of panels, and, as a result of the one or more alerts, the framework module provides data to a dashboard to allow at least one member of a group consisting of (i) selection of one or more of the panels and (ii) creation of another panel that includes data from two or more of the plurality of data sources.

21. The digital data processing system of claim 18, wherein the one or more real-time displays comprise a plurality of panels, and, as a result of the one or more alerts, the framework module provides data to a dashboard to allow at least one member of a group consisting of (i) selection of one or more of the panels and (ii) creation of another panel that includes data from two or more of the plurality of data sources, the two or more data sources being selected based on at least one member of a group consisting of (i) a rule and (ii) a heuristic that caused the one or more alerts to be issued.

22. The digital data processing system of claim 16, wherein the plurality of data sources comprise network nodes at one or more clinical care providers, laboratories, governmental health departments, centers for disease control, and law enforcement offices.

23. The digital data processing system of claim 16, wherein the query functionality comprises any of a graph generator, algorithmic search, and an expert engine.

24. The digital data processing system of claim 16, wherein the plurality of data sources are compliant with a public health information network (PHIN) protocol, a health area network (HAN) protocol, National Electronic Disease Surveillance System (NEDSS) protocol, or other protocol for communication of health at least one member of a group consisting of: (i) health and (ii) bioterrorism data and wherein the query functionality applies requests to, and receives information from, one or more of the plurality of data sources utilizing an API or interface mechanism dictated by the PHIN, HAN or NEDSS or other protocol communication of information used in communication of health and bioterrorism data.

25. The digital data processing system of claim 24, wherein the query functionality applies SQL queries to selected ones of the plurality of data sources.

26. The digital data processing system of claim 17, wherein the criteria specifies a named relationship and a characteristic of that named relationship, and wherein to identify, as related, includes to compare at least one of the relationship and the characteristic named in a criteria with any of
  (a) attributes of the direct ancestor, and
  (b) a relationship between the direct ancestor and any data that descends therefrom, in order to determine whether the director ancestor is in substantial conflict with the criteria.

27. The digital data processing system of claim 16, wherein the framework module generates data to allow display of a border/port security display comprising a plurality of panels, a first of which displays information relating to at least one of the one or more alerts, a second of which displays information from a particular data source or an aggregation of data from several data sources, a third of which displays real-time data from a data source superimposed on a map of a locale.

28. The digital data processing system of claim 25, wherein the framework module generates data to allow a dashboard to respond to a selected user input with respect to an item displayed in one of the panels by displaying additional information about that item.

29. The digital data processing system of claim 28, wherein the framework module generates data to allow a dashboard to respond to an alert by displaying a zoomed-in portion of a locale shown in one of the panels and wherein the system includes additional functionality for alerting people, agencies or other entities of such alert.

30. The digital data processing system of claim 16, configured for any of border & port security, public & community safety, and government data integration applications.

31. A digital data processing system comprising:
  query functionality to (i) apply requests to a plurality of data sources using an application program interface ("API") associated with each of the data sources, wherein at least two of the plurality of data sources utilize different APIs, (ii) receive data from the plurality of data sources in response to the requests and to route that data to a data store,
  the data store to store the data from the plurality of data sources in the form of resource description framework (RDF) triples, where, in a directed graph representation, one or more of the triples are related to one or more others of the triples by any of an ancestor and a descendant relationship,
  an expert engine, coupled to at least member of a group consisting of (i) the plurality of data sources and the query functionality, to execute rules that operate on the RDF triples to identify related data in the data store, the related data including data that match specified criteria or are related thereto, wherein the rules executed by the expert engine include rules to:
    (i) identify, as related, data substantially matching a criteria;
    (ii) identify, as related, data that is a direct ancestor of data identified in any of steps (i), (ii) and (iii), and that is not in substantial conflict with the criteria, wherein step (iii) is set forth below;
    (iii) identify, as related, data (hereinafter "identified descendent") that is a direct descendent of data (hereinafter "identified ancestor") identified as related in any of steps (i), (ii) and (iii), and which identified descendent:
      (a) does not have a named relationship with the identified ancestor substantially matching a relationship named in the criteria, if any;
      (b) is not in substantial conflict with the criteria; and
      (c) does not have a named relationship with the identified ancestor matching a relationship the identified ancestor has with data, if any, as a result of which the identified ancestor was identified during execution of (ii),
  wherein the expert engine is configured to execute the rules to any of (a) trigger further execution of rules and (b) generate alerts; and, a framework module, coupled to the expert engine, to provide data to allow display by one or more displays of information from the data store, as well as one or more alerts resulting from anomalous situations with respect thereto;

wherein the system is configured to perform one or more searches of the plurality of data sources to identify information relevant to the one or more alerts and provide data to display the results of at least one member of a groups consisting of: (i) the one or more searches and (ii) links to those results.

32. The digital data processing system of claim 31, wherein the criteria specifies a named relationship and a characteristic of that named relationship, and wherein to identify, as related, includes to compare at least one of the relationship and the characteristic named in a criteria with any of (a) attributes of the direct ancestor, and (b) a relationship between the direct ancestor and any data that descends therefrom, in order to determine whether the director ancestor is in substantial conflict with the criteria.

33. The digital data processing system of claim 31, wherein the plurality of data sources comprise network nodes at one or more clinical care providers, laboratories, governmental health departments, centers for disease control, and law enforcement offices.

34. The digital data processing system of claim 31, wherein the data provided by the framework module configures a dashboard to provide one or more real-time displays of information from the data store.

* * * * *

UNITED STATES PATENT AND TRADEMARK OFFICE
CERTIFICATE OF CORRECTION

PATENT NO. : 8,572,059 B2
APPLICATION NO. : 10/886515
DATED : October 29, 2013
INVENTOR(S) : Colin P. Britton, Howard Greenblatt and Alan Greenblatt It is certified that error appears in the above-identified patent and that said Letters Patent is hereby corrected as shown below:

In the claims;

Claim 5, col. 19, line 30, "2" should be replaced with --3-- so that the line reads "The digital data processing system of claim 3, wherein".

Claim 17, Col. 21, line 8, the term "groups" should be replaced with --group -- so that the claim reads "The digital data processing system of claim 16, wherein the system is configured to perform one or more searches of the plurality of data sources to identify information relevant to the one or more alerts and provide data to display the results of at least one member of a group consisting of: (i) the one or more searches and (ii) links to those results.".

Signed and Sealed this
Fourth Day of October, 2016

Michelle K. Lee
*Director of the United States Patent and Trademark Office*